(12) United States Patent
Hird et al.

(10) Patent No.: US 12,303,499 B2
(45) Date of Patent: May 20, 2025

(54) AQUEOUS BASED PHARMACEUTICAL FORMULATIONS OF 1,2-DIHYDROPYRIDINE COMPOUNDS

(71) Applicant: Eisai R&D Management Co., Ltd., Tokyo (JP)

(72) Inventors: Geoffrey S. Hird, Chapel Hill, NC (US); Ganesh S. P. Bommareddy, Durham, NC (US); Anjali Joshi, Cary, NC (US); James McShane, Raleigh, NC (US)

(73) Assignee: Eisai R&D Management Co., Ltd., Tokyo (JP)

( * ) Notice: Subject to any disclaimer, the term of this patent is extended or adjusted under 35 U.S.C. 154(b) by 962 days.

(21) Appl. No.: 17/312,077

(22) PCT Filed: Dec. 16, 2019

(86) PCT No.: PCT/US2019/066622
§ 371 (c)(1),
(2) Date: Jun. 9, 2021

(87) PCT Pub. No.: WO2020/124090
PCT Pub. Date: Jun. 18, 2020

(65) Prior Publication Data
US 2022/0023275 A1 Jan. 27, 2022

Related U.S. Application Data

(60) Provisional application No. 62/779,620, filed on Dec. 14, 2018.

(51) Int. Cl.
*A61K 9/08* (2006.01)
*A61K 9/19* (2006.01)
(Continued)

(52) U.S. Cl.
CPC .............. *A61K 31/444* (2013.01); *A61K 9/08* (2013.01); *A61K 9/19* (2013.01); *A61K 47/40* (2013.01)

(58) Field of Classification Search
CPC .......... A61K 31/444; A61K 9/08; A61K 9/19; A61K 47/40; A61K 9/0019; A61K 47/6951; A61P 25/00; A61P 25/28
See application file for complete search history.

(56) References Cited

U.S. PATENT DOCUMENTS 5,356,902 A   10/1994 Ornstein
6,949,571 B2   9/2005 Nagato et al.
(Continued)

FOREIGN PATENT DOCUMENTS

CN   101544599 A   9/2009
CN   104644592 A   5/2015
(Continued)

OTHER PUBLICATIONS

Cydex Pharmaceuticals (What is Captisol®? Product Brochure. https://www.captisol.com/resources. Accessed Jun. 26, 2024.) (Year: 2015).*
(Continued)

*Primary Examiner* — Valerie Rodriguez-Garcia
*Assistant Examiner* — Kyle Nottingham
(74) *Attorney, Agent, or Firm* — Buchanan Ingersoll & Rooney PC

(57) ABSTRACT

An aqueous pharmaceutical formulation of a solubilizing agent with a pyridone compound that is useful as an inhibitor to non-NMDA receptors, particularly to the AMPA receptor is disclosed herein. In some embodiments the pyridone compound is supersaturated in aqueous solution at pH between 6 and 8. The formulations are particularly useful as intravenous injections.

15 Claims, 11 Drawing Sheets

(51) Int. Cl.
*A61K 31/444* (2006.01)
*A61K 47/40* (2006.01)

(56) References Cited

U.S. PATENT DOCUMENTS

| | | | |
|---|---|---|---|
| 7,803,818 | B2 | 9/2010 | Omae et al. |
| 8,304,548 | B2 | 11/2012 | Kayano et al. |
| 2007/0142640 | A1 | 6/2007 | Arimoto et al. |
| 2010/0099714 | A1 | 4/2010 | Yoshino et al. |
| 2010/0324297 | A1 | 12/2010 | Arimoto et al. |
| 2016/0228454 | A1 | 8/2016 | Zhang et al. |

FOREIGN PATENT DOCUMENTS

| | | |
|---|---|---|
| CN | 104706604 A | 6/2015 |
| CN | 106389367 A | 2/2017 |
| CN | 107427458 A | 12/2017 |
| DE | 19643037 A1 | 4/1998 |
| EP | 0802195 A2 | 10/1997 |
| RU | 2358733 C2 | 6/2009 |
| WO | 9425469 A1 | 11/1994 |
| WO | 9501357 A1 | 1/1995 |
| WO | 9610023 A1 | 4/1996 |
| WO | 9718163 A1 | 5/1997 |
| WO | 9728135 A1 | 8/1997 |
| WO | 9734878 A1 | 9/1997 |
| WO | 9743276 A1 | 11/1997 |
| WO | 9838173 A1 | 9/1998 |
| WO | 9855480 A1 | 12/1998 |
| WO | 0001376 A2 | 1/2000 |
| WO | 03047577 A2 | 6/2003 |
| WO | 2014034756 A1 | 3/2014 |
| WO | 2016127170 A1 | 8/2016 |
| WO | 2018169798 A1 | 9/2018 |

OTHER PUBLICATIONS

Specification for U.S. Appl. No. 62/738,833, filed Sep. 28, 2018. (Year: 2018).*

Chaomei, C. et al."Beijing, China Press of Traditional Chinese Medicine" Cataloging-in-Publication (CIP) data, Innovative textbooks for national colleges and universities of traditional Chinese medicine in the new century, Oct. 2008, selected pages.

International Search Report (PCT/ISA/210) and Written Opinion (PCT/ISA/237) mailed on Mar. 20, 2020, by the European Patent Office as the International Searching Authority for International Application No. PCT/US2019/066622.

Office Action issued on Jun. 7, 2023, by the Russian Patent Office in corresponding Russian Patent Application No. 2021116836/04 (035442), and an English Translation of the Office Action. (26 pages).

* cited by examiner

| Diluents | pH of Diluted Solution | Appearance by Visual Observation under Tyndall Beam |
|---|---|---|
| Water | 2.94 | Visually clear for at least 4 days |
| Normal Saline (NS) | 2.88 |  |
| 5% Dextrose (D5W) | 2.89 | |
| 7.5% Sodium Bicarbonate | 8.63 | |
| Lactated Ringer's (LR) | 4.74 | |

AQUEOUS BASED PHARMACEUTICAL FORMULATIONS OF 1,2-DIHYDROPYRIDINE COMPOUNDS

CROSS-REFERENCE TO RELATED APPLICATIONS

This application claims the benefit of U.S. provisional patent application No. 62/779,620, filed on Dec. 14, 2018. That application is incorporated by reference as if fully rewritten herein.

BACKGROUND

Described herein is an aqueous based pharmaceutical formulation of a pyridone compound useful as an inhibitor to non-NMDA receptors, particularly to the AMPA receptor.

Glutamate and aspartate are important amino acids in nerve functions. These include recognition, memory, movement, respiration, cardiovascular adjustment and sensation. Glutamate and aspartate are often referred to as excitatory neurotransmitters due to their ability to increase the probability that a target cell will fire an action potential following receptor binding. Two types of receptors—an ion channel type and a G-protein coupled type—are known. The former is further classified into N-methyl-D-aspartate (NMDA) receptor, α-amino-3-hydroxy-5-methyl-4-isoxazole propionic acid (AMPA) receptor, kainate receptor, and other receptors.

Excitatory neurotransmitters have been known to induce neurotoxicity by, for example, abnormal excitation of central nerves, a process known as excitotoxicity. It has been noted that excitotoxicity is often related to the death of nerve cells caused by various nervous diseases. These nervous diseases include cerebral ischemia, head injury, spinal cord injury, Alzheimer's disease, Parkinson's disease, amyotrophic lateral sclerosis (ALS), Huntington's chorea, AIDS nervous disturbance, epilepsy, neurodegeneration observed after the state of hypoxia, mental disorder, mobility disturbance, pain, spasticity, nervous disturbance by toxin in food, various neurodegenerative diseases, various mental diseases, chronic pain, migraine, cancer pain, and pain caused by diabetic nervous disturbance. These are serious diseases where many mechanisms of onset have not been clarified and pharmaceutical agents effective for therapy are unknown.

Many nervous system diseases are closely related to excessive release or accumulation of excitatory neurotransmitters and/or changes in the expression pattern of receptors. For example, glutamate concentration in cerebrospinal fluid and plasma increases in stroke, cerebral ischemia, head injury and spinal cord injury (Castillo, J., Dazalos, A. and Noya, M., 346 Lancet, 79-83 (1997)). Glutamate, NMDA, AMPA, kainite, and others cause neuropathy when excessively applied to nerve cells (Meldrum, B., 18 Brain Res. Reviews, 293 (1993)). In Alzheimer's disease, β-amyloid protein enhances the neurotoxicity of glutamate and promotes the release of glutamate (Arias, C., Arrieta, I. and Tapia, R., 41 J. Neurosci. Res. 561-566 (1995)). In Parkinson's disease, L-DOPA hydroxide activates the AMPA receptor (Cha, J. J., et al., 132 Neurosci. Lett. 55-58 (1991)) and enhances neurotoxicity (Olney, J., et al. 108(3) Exp. Neurol. 269-272 (1990); Rosenberg, P. A., et al., 88 Proc. Natl. Acad. Sci. USA 4865-4869 (1991)). L-DOPA also promotes the generation of free radicals, resulting in a rise of oxidative stress (Smith, T. S., et al., 5 Neuroreport, 1009-1011 (1994)). In Huntington's chorea, a substance which inhibits the release of glutamate is reportedly effective at improving symptoms. In ALS, many reports show the participation of glutamate in its pathology. There are some cases where AIDS patients suffer from recognition nerve function deficiency and participation of glutamate is suggested. For example, it has been shown that gp120, a glycoprotein in the envelope of the HIV virus, suppresses the uptake of glutamate by astrocytes (Dreyer, E. B., 7 Eur. J. Neurosci. 2502-2507 (1995); Ushijima, H., et al., 7 Eur. J. Neurosci. 1353-1359 (1995)) while a substance which inhibits the release of glutamate suppresses the neurodegeneration by gp120 (Sindou, P., et al., 126 J. Neurosci. 133-137 (1994); Muller, W. E. G., et al., 226 Eur. J. Pharmacal. Molec. Pharmacal. 209-214 (1992); Lipton, S. A., 42 Neurology, 1403-1405 (1992)).

In allergic encephalomyelitis, in mice exhibiting inflammation, an enzyme that decomposes glutamate incorporated from outside of the cell is deficient (Hardin-Pouzet, H., 20 Glia. 79-85 (1997)). Olivopontocerebellar atrophy (OPCA) is a disease sometimes combined with Parkinson's disease. Autoantibodies to GluR2 (a subunit of the AMPA receptor) discovered in diseased individuals suggests a connection between OPCA and the AMPA receptor (Gahring, L. C., 48(2) Neurology 494-500 (1997)). Regarding epilepsy, mice unable to construct the GluR2 subunit of the AMPA receptor show an increase in $Ca^{2+}$ permeability of the AMPA receptor that can cause death (Brusa, R., 270 Science 1677-1680 (1995)). In addition, NBQX (2,3-Dioxo-6-nitro-1,2,3,4-tetrahydrobenzo[f]quinoxaline-7-sulfonamide) (Sheardown, et al., 247 Science 571 (1990)) and other inhibiting compounds to AMPA receptors have antianxiety and anticonvulsant action (Turski, L., et al., 260 J. Pharmacal. Exp. Ther. 742 (1992); Kotlinska, J., et al. 60(1) Pharmacal. Biochem. Behavior 119-124 (1998)). There are also reports of a connection between the AMPA receptor/kainate receptor and urinary disturbance, drug abuse, pain, and other disorders (Yoshiyama, M., et al. 280(2) J. Pharmacol. Exp. Ther. 894-904 (1997); Gray, A., et al., 268(3) Neuroscience Letters 127-130 (1999)).

Substances showing an antagonistic action to excitatory neurotransmitter receptors may be useful for therapy of the above-mentioned nerve diseases. Antagonists to the non-NMDA receptors, such as the AMPA receptor or kainate receptor, are particularly attractive. For example, International Patent Application Publication No. WO 00/01376 reports that inhibitors of the interaction of glutamate with the AMPA and/or kainate receptor complex are useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchiafava-Bignami disease, central-pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, and isolated cerebral vasculitis.

Competitive AMPA receptor-inhibiting compounds and non-competitive AMPA receptor inhibiting compounds are reported in U.S. Pat. No. 6,949,571. Competitive AMPA receptor-inhibiting compounds having a quinoxalinedione skeleton are reported in International Patent Application Publication Nos. WO 94/25469 and WO 96/10023, and U.S. Pat. No. 5,356,902. There are reports on non-competitive AMPA receptor-inhibiting compounds in International Patent Application Publication Nos. WO 95/01357, WO 97/28135, WO 97/18163, WO 97/43276, WO 97/34878, WO 98/38173, and European Patent No. EP 802195 and German Patent No. DE 19643037.

Compounds that have shown excellent AMPA receptor and/or kainate receptor inhibitory activity include the 1,2-dihydropyridine compounds. International Patent Application Publication No. WO 98/55480 identifies compounds represented by formula (a) as a ligand for $GABA_A\alpha$ subunit.

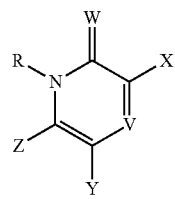

(a)

In formula (I), R is a hydrogen atom, a $C_{1-6}$ alkyl group, a $C_{2-6}$ alkenyl group, a $C_{2-6}$ alkynyl group, or a $C_{1-6}$ alkoxy group; V is CH or N; W is O or S; X is a phenyl group which is unsubstituted or substituted with one or more group(s) selected from a $C_{1-6}$ alkyl group, $CF_3$, a cyano group, a nitro group, a halogen, or an aromatic hetero group which is substituted with one or more group(s) selected from a $C_{1-6}$ alkyl group, $CF_3$, or a halogen; Y is a hydrogen atom, a $C_{1-6}$ alkyl group, a $C_{2-6}$ alkenyl group, a $C_{2-6}$ alkynyl group, or an aryl group; and Z is halogen, a $C_{3-6}$ cycloalkyl group, a $C_{1-6}$ alkylthio group, a $C_{2-6}$ alkenylthio group, or an aryl group. International Patent Application Publication No. WO 00/07988 identifies compounds represented by formula (b) as a useful for therapy for epilepsy.

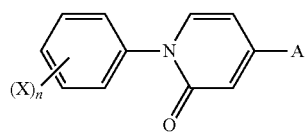

(b)

In formula (b), n is 0, 1, 2, 3, 4 or 5; X is a hydrogen atom, a $C_{1-4}$ alkyl group, a $C_{1-4}$ alkoxy group, a trifluoromethyl group, a trifluoromethoxy group, or a halogen; A is an amino group, a $C_{1-4}$ alkylamino group, a $C_{1-4}$ dialkylamino group, a morpholino group, a piperidino group, or a pyrrolidino group. However, the connection of compounds of formula (b) with the AMPA receptor or the kainate receptor is unknown. Additionally, compounds which inhibit the AMPA receptor and/or the kainate receptor and could be used as aqueous based pharmaceutical agents have not yet been identified.

BRIEF SUMMARY

We report a pharmaceutical formulation including a solubilizing agent and a therapeutically effective amount of a compound represented by the following formula (I),

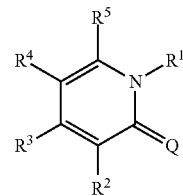

(I)

wherein Q is O, $R^3$ and $R^5$ are the same as or different from each other and each indicates a hydrogen atom or a $C_{1-6}$ alkyl group; and $R^1$ indicates a $C_{3-8}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, and $R^2$ and $R^4$ are the same as or different from each other and each indicates a group represented by the formula —X-A wherein X indicates a single bond and A indicates a $C_{3-6}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively. The compound and solubility agent may be present in a ratio whereby dilution of the formulation in an aqueous medium provides the compound in a supersaturated solution. This may occur, for example, following reconstitution from a lyophilized preparation. In at least one embodiment a formulation is capable of delivering from about 0.5 to about 24 milligrams of said compound parenterally, for example, intravenously.

Suitable solubilizing agents may be a cyclodextrin or combination of more than one cyclodextrin. Suitable cyclodextrins include, for example, α-cyclodextrin, β-cyclodextrin, and hydroxypropyl β-cyclodextrin, and sulfobutyl ether β-cyclodextrin. In one embodiment the compound is perampanel, which is an anti-epileptic drug. Perampanel is described chemically as 2-(6'-oxo-1'-phenyl-1',6'-dihydro[2,3'-bipyridin]-5'-yl)benzonitrile. One source of a hydrate of perampanel is FYCOMPA™ (Perampanel; Eisai Co., Ltd., Tokyo), described chemically as 2-(2-oxo-1-phenyl-5-pyridin-2-yl-1,2-dihydropyridin-3-yl) benzonitrile hydrate (4:3). The molecular formula of FYCOMPA brand perampanel is $C_{23}H_{15}N_3O·¾H_2O$ and the molecular weight is 362.90 (¾ hydrate). In some embodiments the molar ratio of sulfobutyl ether β-cyclodextrin to perampanel is between 28 and 108. In some embodiments it is between 50 and 75.

Polymorphs of perampanel also exist (see, e.g., U.S. Pat. No. 8,304,548, published as United States Patent Application Publication No. 2010/0324297, the disclosures of which hereby are incorporated by reference in their entirety). The compound may be in the amorphous phase (see, e.g., U.S. Pat. No. 7,803,818, the disclosure of which is hereby incorporated by reference in its entirety). The compound may be in solution. That solution may be an aqueous solution. The formulation may be lyophilized. In some embodiments the formulation is lyophilized at a concentration that is below the level necessary for supersaturation of the compound, then reconstituted in aqueous solution at a concentration that reaches supersaturation.

Embodiments may also provide a storage-stable aqueous pharmaceutical formulation for intravenous administration including an aqueous, supersaturated perampanel solution and sulfobutyl ether β-cyclodextrin. The perampanel and said sulfobutyl ether β-cyclodextrin may be present, for example, in a molar ratio of moles sulfobutyl ether β-cyclodextrin to moles perampanel of between 60 and 110. The aqueous medium may have a pH between 2.5 and 9, and in some embodiments between 6 and 8. The amount of solubilizing agent, by weight to volume, may be between 0.005% and 60%. In some embodiments the amount is between 3% and 9.5%.

Further embodiments may provide a process for preparing a pharmaceutical formulation in an aqueous medium comprising a solubilizing agent and a therapeutically effective amount of a compound represented by the following formula,

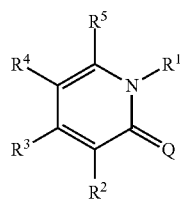

wherein Q indicates O, $R^3$ and $R^5$ are the same as or different from each other and each indicates a hydrogen atom or a $C_{1-6}$ alkyl group; and $R^1$ indicates a $C_{3-8}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, and $R^2$ and $R^4$ are the same as or different from each other and each indicates a group represented by the formula —X-A wherein X indicates a single bond and A indicates a $C_{3-6}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, including the steps of
  a) solubilizing the compound at acidic pH in a solubilizing agent, and
  b) adjusting the pH to between 6 and 8 with the addition of a diluent.

The solubilizing agent may be a cyclodextrin. For example, it may be α-cyclodextrin, β-cyclodextrin, and hydroxypropyl β-cyclodextrin, and sulfobutyl ether β-cyclodextrin. The solubilizing agent may also be a mixture of cyclodextrins. The compound may be perampanel.

Further embodiments provide a method of treating a neurodegenerative disease with a pharmaceutical formulation in an aqueous medium comprising a solubilizing agent and a therapeutically effective amount of a compound represented by the following formula,

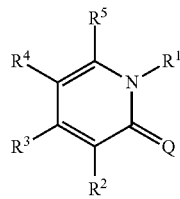

wherein Q indicates O, $R^3$ and $R^5$ are the same as or different from each other and each indicates a hydrogen atom or a $C_{1-6}$ alkyl group; and $R^1$ indicates a $C_{3-8}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, and $R^2$ and $R^4$ are the same as or different from each other and each indicates a group represented by the formula —X-A wherein X indicates a single bond and A indicates a $C_{3-6}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, including the steps of
  a) identifying a patient in need thereof, and
  b) administering a therapeutically effective amount of said pharmaceutical formulation in an aqueous medium.

The solubilizing agent may be, for example, one of α-cyclodextrin, β-cyclodextrin, hydroxypropyl β-cyclodextrin, and sulfobutyl ether β-cyclodextrin. The compound may be perampanel. In some embodiments the administration is conducted using materials not made of polyvinyl chloride (PVC). The pH of the pharmaceutical formulation may, for example, be between 6 and 8.

BRIEF DESCRIPTION OF THE FIGURES

FIG. 1 is adapted from Sangwal, K., "Novel Approach to Analyze Metastable Zone Width Determined by the Polythermal Method: Physical Interpretation of Various Parameters' Crystal Growth & Design" 2009, Vol 9(2), 942-950.

The points represent the individual data points where precipitation occurs at the different cooling rates. The mesh is the surface that is fitted to the data.

Figure 11:
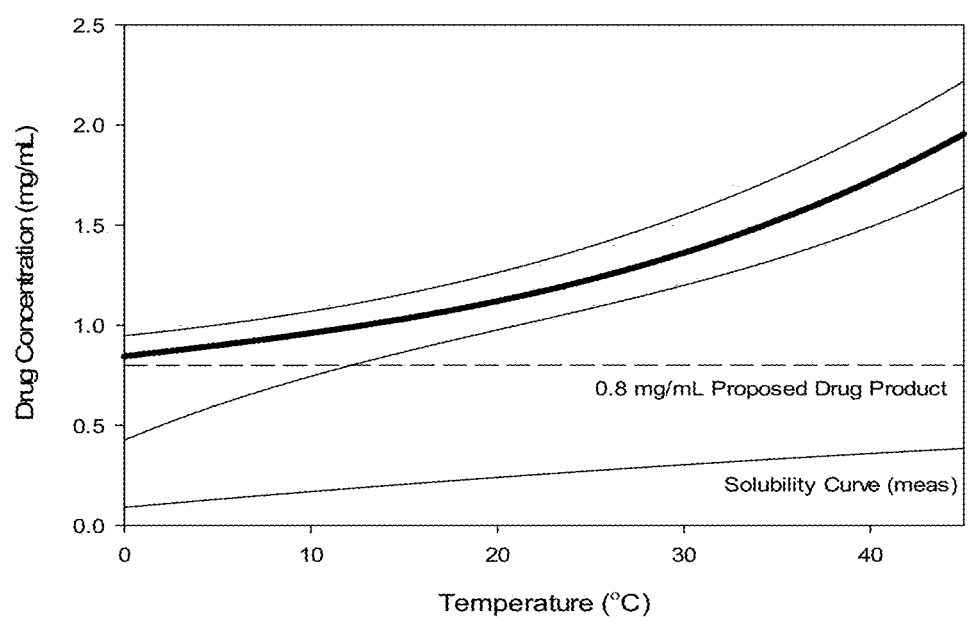

FIG. 11 shows a metastable zone boundary (with 95% confidence intervals) for a sample in a 40% SBE-β-CD, pH 7 Solution. The solubility curve of the sample and the proposed DP conc. are added to the plot for reference

DETAILED DESCRIPTION

Embodiments as reported herein include storage-stable aqueous pharmaceutical formulations for intravenous administration. Embodiments include a therapeutically effective amount of a compound represented by the following formula (I),

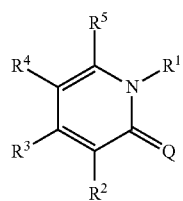

(I)

wherein Q is O, $R^3$ and $R^5$ are the same as or different from each other and each indicates a hydrogen atom or a $C_{1-6}$ alkyl group; and $R^1$ indicates a $C_{3-8}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, and $R^2$ and $R^4$ are the same as or different from each other and each indicates a group represented by the formula —X-A wherein X indicates a single bond and A indicates a $C_{3-6}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively.

Figure 1:
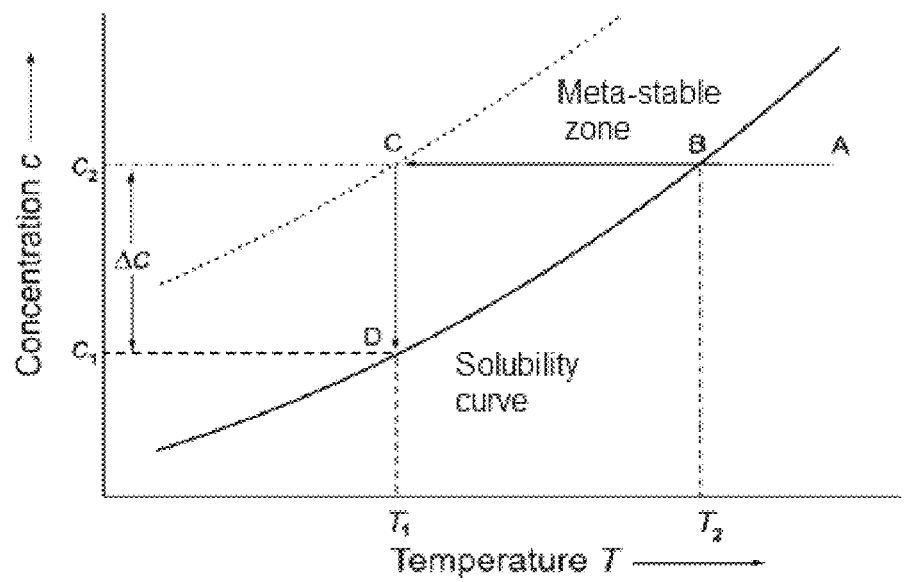
FIG. 1 is a schematic illustration of the basis of determination of the maximum supercooling $\Delta T_{max}$ in the polythermal method of metastable zone width.

In some embodiments, the compound of Formula (I) is supersaturated in the aqueous formulation; that is, it is present in a concentration above its solubility limit. In some embodiments this occurs after reconstitution (if lyophilized) and dilution into aqueous medium. When supersaturated the compound is in a metastable state in which the compound will not precipitate from solution unless a seed is added to cause nucleation and precipitation. Solubility and metastable zone width curves summarize and graphically represent the range of conditions under which crystals will grow and those conditions that will result in primary nucleation. FIG. 1 depicts an example of a solubility curve as a function of temperature and a corresponding metastable zone. In FIG. 1, the temperature is on the horizontal axis and the concentration of the material is on the vertical axis of the graph. The bold line in FIG. 1 is the solubility curve. A solubility curve indicates the solid-liquid thermodynamic equilibrium concentration of a substance in a solvent system, as a function of temperature. It is also referred to as the clear point curve, as it can be obtained experimentally by heating a slurry of material in a solvent system until complete dissolution is obtained, resulting in a clear solution (the clear point). Crystals will grow at concentrations above the solubility curve.

The dotted line in FIG. 1 is the metastable zone boundary. The metastable zone boundary indicates the concentration of a substance in a solvent system above which primary nucleation occurs, as a function of temperature. It is also referred to as the "cloud point curve," as it can be obtained experimentally by cooling a saturated solution at a fixed rate until nucleation occurs and the solution becomes cloudy (the cloud point). At concentrations above the metastable zone boundary, spontaneous crystallization, i.e. primary nucleation, will occur.

Embodiments may include suitable amounts of a compound of Formula (I) to deliver a desired amount of the compound to a patient in need of treatment. For example, in one embodiment, a formulation is capable of delivering from about 0.5 to about 24 milligrams of the compound to a human parenterally, for example, intravenously, in a single course of administration.

The aqueous-based formulations also include a solubilizing agent. In some embodiments the solubilizing agent is Sulfobutyl Ether Beta Cyclodextrin (SBE-β-CD). One brand of SBE-β-CD that is useful is CAPTISOL® brand SBE-β-CD, available from Ligand Pharm., Inc., of California. Other solubilizing agents may be useful, including other cyclodextrin family members. Additional solubilizing agents that may be used include ethanol, macrogol, propylene glycol, polysorbate, glycerin, polyethoxylated hydrogenated castor oil, ethanol amine, poloxamer F68, sodium gluconate, nicotinamide, urea, dextran, sodium lactate, arginine, glycine, sodium sulfite, sodium carbonate, sodium acetate, sodium benzoic acid, magnesium chloride, sodium salicyclic acid, sodium hydrogen sulfite, ethylenediaminetetraacetic acid, hydroxypropyl beta cyclodextrin, cycloamyloses, and others. In some embodiments only a single solubilizing agent is present. For example, only SBE-β-CD is used. In other embodiments multiple solubilizing agents are present.

Formulations may contain additional components. One optional component is a buffer. Suitable buffers include, for example, but are not limited to, buffers that are acceptable for parenteral use from between pH 2-11. Suitable buffers include acetate, ammonium, ascorbate, benzoate, bicarbonate, citrate, phosphate, diethanolamine, glycine lactate, succinate, tartrate, tromethamine, and others. When the formulation is to be lyophilized, one or more buffers may be added up to an amount, by total weight of the pre-dilution composition, that would inhibit proper freezing in a lyophilized formulation.

Methods for synthesizing compounds of Formula (I) are reported in U.S. Pat. No. 6,949,571, the disclosure of which hereby is incorporated by reference in its entirety. A representative example of a compound of Formula (I) is 2-(6'-oxo-1'-phenyl-1',6'-dihydro[2,3'-bipyridin]-5'-yl)benzonitrile. This is also known as "perampanel." Perampanel is available, for example, as FYCOMPA from Eisai Co., Ltd., Tokyo. FYCOMPA brand perampanel is 2-(2-Oxo-1-phenyl-5-pyridin-2-yl-1,2-dihydropyridin-3-yl)benzonitrile hydrate (4:3). The molecular formula of FYCOMPA perampanel is $C_{23}H_{15}N_3O \cdot \text{¾}H_2O$ and the molecular weight is 362.90 (¾ hydrate). The structure of perampanel is illustrated below:

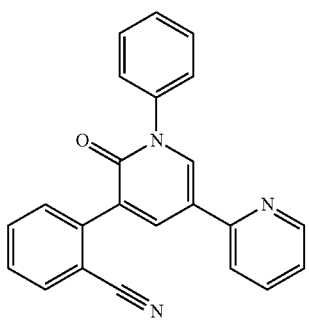 [SMILES: N#Cc1ccccc1-c1cc(-c2ccccn2)cn(-c2ccccc2)c1=O]

Perampanel has particularly poor water solubility. Perampanel has an aqueous solubility of about 0.001 mg/mL at pH 7 at ambient room temperature. Many attempts to solubilize perampanel in water have failed. The formulation described herein demonstrates a supersaturated state that is unexpectedly metastable.

As used herein, "acute neurodegenerative disease" can be, for example, cerebrovascular disorders at acute stage (subarachnoid hemorrhage, cerebral infarction and the like), head injury, spinal cord injury, and neuropathies due to hypoxia or hypoglycemia. "Chronic neurodegenerative disease," for example, can be Alzheimer's disease, Parkinson's disease, Huntington's chorea, amyotrophic lateral sclerosis, spinocerebellar degeneration, epilepsy, status epilepticus, and the like. "Infectious encephalomyelitis" can be, for example, HIV encephalomyelitis, and a "demyelinating disease" can be encephalitis, acute disseminated encephalomyelitis, multiple sclerosis, acute polyradiculoneuritis, Guillain-Barre syndrome, chronic inflammatory demyelinating polyneuropathy, Marchifava-Bignami disease, central pontine myelinolysis, neuromyelitis optica, Devic disease, Balo disease, HIV myelopathy, HTLV myelopathy, progressive multifocal leukoencephalopathy, secondary demyelinating disease and the like. A "secondary demyelinating disease" can be CNS lupus erythematodes, polyarteritis nodosa, Sjoegren's syndrome, sarcoidosis, isolated cerebral vasculaitis and the like.

As used herein, the term "therapeutically effective amount" refers to an amount that is used for repairing neurodegeneration due to neurodegenerative disease, and recovering neural function in subject in need thereof. For those skilled in the art, the therapeutically effective amount, as well as dosage and frequency of administration may be determined according to their knowledge and standard methodology of routine experimentation. The term "and/or" as used herein means that both cases in case of "and" and in case of "or" are included.

Incidentally, although the structural formula of a compound may express a certain isomer for the sake of convenience, this disclosure covers all isomers such as geometrical isomers resulting from the structure of the compound, optical isomers due to asymmetric carbon, rotamers, stereo isomers and tautomers, as well as a mixture of isomers, and is not limited to the description of the formula given for the sake of convenience but may be another isomer or may be a mixture. Accordingly, although it is possible that an asymmetric carbon atom is present in a molecule, and that optically active substances and racemic substances may be present, this disclosure is not limited thereto but covers any of them. Further, crystal polymorphism may be present but, again, there is no limitation as to any of the single crystal forms or mixtures of forms. The compound (I) or its salt may be an anhydride or a hydrate, and either of them is envisioned. The metabolite which is generated by decomposing the compound (I) related to the present invention in vivo, and the prodrug of the compound (I) or its salt related to the present invention produce are also envisioned. Although specific hydrates of perampanel are discussed in this application, embodiments should not be construed to limit to any particular hydrate unless otherwise stated.

There is no particular limitation for "a salt" in the specification of the present application so far as it forms a salt with the compound of the present invention and is a pharmacologically acceptable one. Embodiments include salt with a hydrogen halide (such as hydrofluoride, hydrochloride, hydrobromide or hydroiodide), salt with an inorganic acid (such as sulfate, nitrate, perchlorate, phosphate, carbonate or bicarbonate), salt with an organic carboxylic acid (such as acetate, trifluoroacetate, oxalate, maleate, tartrate, fumarate or citrate), salt with an organic sulfonic acid (such as methanesulfonate, trifluoromethanesulfonate, ethanesulfonate, benzenesulfonate, toluenesulfonate or camphorsulfonate), salt with an amino acid (such as aspartate or glutamate), salt with a quaternary amine, salt with an alkaline metal (such as sodium salt or potassium salt) and salt with an alkaline earth metal (such as magnesium salt or calcium salt). Additional embodiments include examples of the "pharmacologically acceptable salt" such as hydrochloride, oxalate, mesylate, etc. and others known in the art. See, for example, Gibson, M., Ed. (2004). Pharmaceutical Preformulation and Formulation A Practical Guide from Candidate Drug Selection to Commercial Dosage Form. New York, Interpharm/CRC., the disclosure of which relating to pharmaceutically acceptable salts is hereby incorporated by reference in its entirety.

As used herein, the term "halogen atom" indicates fluorine, chlorine, bromine, iodine and the like. The term "$C_{1-6}$ alkyl group" indicates an alkyl group having 1 to 6 carbons, and examples include linear chain or branched chain alkyl groups such as methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group, and the like.

The term "$C_{2-6}$ alkenyl group" indicates an alkenyl group having 2 to 6 carbons, and examples include vinyl group, allyl group, 1-propenyl group, 2-propenyl group, iso-propenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group, 1,6-hexadienyl group, and the like.

The term "$C_{3-6}$ alkynyl group" indicates an alkynyl group having 2 to 6 carbons, and examples include ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexadiynyl group, 1,6-hexadiynyl group, and the like.

The term "$C_{1-6}$ alkoxy group" indicates an alkoxy group having 1 to 6 carbons, and examples include methoxy group, ethoxy group, n-propoxy group, isopropoxy group, secpropoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropoxy group, 1,2-dimethylpropoxy group, 2,2-dimethylpropoxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1, 3-dimethylbutoxy group, 2-ethylbutoxy group, 1,3-dimethylbutoxy group, 2-methylpentoxy group, 3-methylpentoxy group, hexyloxy group, and the like.

The term "$C_{2-6}$ alkenyloxy group" indicates an alkenyloxy group having 2 to 6 carbons, and examples include vinyloxy group, allyloxy group, 1-propenyloxy group, 2-propenyloxy group, iso-propenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexadienyloxy group, 1,6-hexadienyloxy group, and the like.

The term "$C_{3-8}$ cycloalkyl group" indicates a cycloalkyl group composed of 3 to 8 carbon atoms, and examples include cyclopropyl group, cyclobutyl group, cyclopentyl group, cyclohexyl group, cycloheptyl group, cyclooctyl group, and the like.

The term "$C_{3-8}$ cycloalkenyl group" indicates a $C_{3-8}$ cycloalkenyl group composed of 3 to 8 carbon atoms, and examples include cyclopropen-1-yl, cyclopropen-3-yl, cyclobuten-1-yl cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl, 1,3,6-cyclooctatrien-6-yl group, and the like.

The term "5 to 14 membered non-aromatic heterocyclic group" means a mono-cyclic type, di-cyclic type, or tri-cyclic type 5 to 14 membered non-aromatic heterocyclic group which contains one or more of hetero atoms selected from a group which consists of nitrogen atom, sulfur atom and oxygen atom. Specific examples in the group include, for example, pyrrolidinyl group, pyrrolyl group, piperidinyl group, piperazinyl group, imidazolyl group, pyrazolidyl group, imidazolidyl group, morpholyl group, tetrahydrofuryl group, tetrahydropyranyl group, pyrrolinyl group, dihydrofuryl group, dihydropyranyl group, imidazolinyl group, oxazolinyl group, and the like. Further, a group derived from a pyridone ring and a non-aromatic condensed ring (for example, a group derived from a phthalimide ring, a succinimide ring, and the like) are also included in the non-aromatic heterocyclic group.

The term "$C_{6-14}$ aromatic hydrocarbocyclic group" and "aryl group" mean an aromatic hydrocarbocyclic group having which is composed of 6 to 14 carbon atoms, and a mono-cyclic group, and a condensed group of a di-cyclic group, a tri-cyclic group and the like. Specific examples in the group include phenyl group, indenyl group, 1-naphthyl group, 2-naphthyl group, azulenyl group, heptalenyl group, biphenyl group, indathenyl group, acenaphthyl group, fluorenyl group, phenalenyl group, phenanthrenyl group, anthracenyl group, cyclopentacyclooctenyl group, benzocyclooctenyl group, and the like.

The term "5 to 14 membered aromatic heterocyclic group" and "heteroaryl group" mean a mono-cyclic type, di-cyclic type, or tri-cyclic type 5 to 14 membered aromatic heterocyclic group which contains one or more of hetero atoms selected from a group which consists of nitrogen atom, sulfur atom and oxygen atom. For example, specific examples in the group include 1) aromatic heterocyclic groups containing nitrogen such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, iso-indolyl group, indolizinyl group, prenyl group, indazolyl group, quinolyl group, iso-quinolyl group, quinoliziyl group, phthalazyl group, naphthylidinyl group, quinoxalyl group, quinazolinyl group, cynnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, pyrazolopyridinyl group, pyrazolopyridinyl group, and the like; 2) aromatic heterocyclic groups containing sulfur such as thienyl group or benzothienyl group; 3) aromatic heterocyclic groups containing oxygen such as furyl group, pyranyl group, cyclopentapyranyl group, benzofuryl group or iso-benzofuryl group; and 4) aromatic heterocyclic groups containing 2 or more of different hetero atoms such as thiazolyl group, iso-thiazolyl group, benzothiazolyl group, benzthiadiazolyl group, phenothiazinyl group, isoxazolyl group, furazanyl group, phenoxazinyl group, oxazolyl group, isoxazoyl group, benzoxazolyl group, oxadiazolyl group, pyrazoloxadiazolyl group, imidazothiazolyl group, thienofuranyl group, furopyrrolyl group or pyridoxadinyl group.

The term "storage stable" means that a formulation does not undergo precipitation in the absence of seeding upon storage at 20° C. for at least one day. The term "induction time" means the elapsed time of a fluid prior to the appearance of precipitate.

The relative amount of the compound of Formula (I) in a formulation can vary over a wide range. It may depend on a variety of factors including, but not limited to, the identity of the compound, the activity of the compound for a particular disorder being treated, and the intended mode of administration.

In one embodiment the amount of a compound of Formula (I) in a formulation most often ranges from about 0.5 to 24 mg diluted into a volume of between 50 and 100 mL. In many embodiments, the amount of the compound in the formulation is relative to the amount of solubilizer that is also in the formulation.

Any pharmaceutically acceptable aqueous medium, such as water of sufficiently high purity, may be used in the formulations. This includes the use of sterile, nonpyrogenic, distilled water, or water for injection. In one method of preparation, the SBE-β-CD is dissolved in water for injection. The pH of the solution is then lowered to an acidic level and perampanel is dissolved in the solution. Filtration of the acidic perampanel solution may be performed to remove nucleation sites at this time. The pH of the solution is then raised to a neutral pH, and water for injection is added to achieve a final volume. In one embodiment, the pH of the solution is lowered to an acidic level with phosphoric acid. In another embodiment, the pH is raised to a neutral pH with sodium hydroxide.

Typically, the final solution is filtered and dried. Filtration may take place, for example, through a 0.22 μm filter. By filtering the formulation one may avoid the presence of nuclei that would seed crystal formation when the formulation is reconstituted and diluted to a neutral (or approximately neutral) pH. The formulation may be dried to eliminate any solvent that is used in the preparation of the formulation prior to reconstitution and dilution with aqueous medium. The solvent may be any of the known solubilizing agents including tert-butyl alcohol.

Drying can be carried out by any known method such as spray drying, sterile spray-drying, fluidized bed granulation, freeze drying, lyophilization, tray drying or the like, and either one method or a combination of multiple methods may be used, but these examples are not limiting. In the case of sterile spray-drying, a fine particle-containing composition can be obtained by spray-drying the fine particle dispersion with a spray dryer or the like.

In the case of fluidized bed granulation, a fine particle-containing composition is obtained by spraying and granulating the fine particle dispersion of the present invention on a cyclodextrin, lactose, starch or other powder. In the case of freeze drying (also known as lyophilization), the fine particle-containing composition is obtained by adding a sugar or other tonicity agent to the fine particle dispersion, and then using a freeze dryer to remove the solvent by freezing at generally from −20° C. to −60° C. In the case of tray drying, a fine particle-containing composition is obtained by drying the fine particle dispersion at generally from 50° C. to 80° C., either as is or after adsorption of the solvent with an excipient. Following drying, the fine particle-containing composition may be powder filled into a vial, or may be reconstituted in water and converted from a crystalline to an amorphous state.

The pH of the formulation may be maintained after dilution to provide long-term stability of the formulation at room temperature. According to one aspect, the compound is solubilized at acidic pH in combination with a high concentration of solubilizing agent. This allows dissolution of a substantial amount of the compound. The formulation is then diluted to a neutral pH in combination with solubilizing agent. The pH range of the formulation can vary from 1.5 to 8.0 and the range of solubilizing agent can vary from 20% to 50%. Typical embodiments that include an aqueous diluent have a pH between 1 to 10 with a range of solubilizing agent of 3% to 9.5%. Other embodiments may have a pH between 6 and 8. Administered formulations also show acceptable tonicity and pH for intravenous infusion.

The formulations may be packaged and administered via any suitable route of parenteral administration. Formulations for intravenous injection may be packaged, for example, in a glass vial, in a pre-filled syringe, or in an ampule. In one embodiment, the formulations are not packaged or administered with components made from polyvinyl chloride (PVC), but are packaged or administered with components which have polyethylene (PE) or glass surfaces. The formulations may be administered with standard intravenous (I.V.) diluent solutions, e.g., D5W, normal saline, custom diluents, or Lactated Ringer's solution.

Suitable dosages can be ascertained depending on such factors as the identity of the compound and the type of the disorder being treated. As will be apparent to persons skilled in the art, dose of the pharmaceutical agent varies depending upon degree of symptom, age, sex, body weight, dosage form, sensitivity to the pharmaceuticals, etc. In the case of adults, the daily dose is usually about 30 μg to 1 g, but may be 100 μg to 500 mg, or 100 μg to 30 mg. This may be administered once daily or in several portions a day. Additional dosage regimens may be used as determined appropriate by a physician for treating a particular disorder. The current FYCOMPA product has FDA approved daily dosages of 2 mg, 4 mg, 6 mg, 8 mg, 10 mg and 12 mg. The FDA Approved labeling and package insert is hereby incorporated by reference in its entirety, in particular the information regarding "Dosage and Administration" and Dosage Forms and Strengths." In an embodiment, the parenteral formulations would contain sufficient amounts of the active ingredient, e.g., perampanel, to achieve the same or similar in vivo efficacy in treating a particular disorder.

EXAMPLES

The following examples are provided for illustrative purposes only and should not be construed to limit the scope of the appended claims whatsoever.

Example 1: Solubility Studies

Figure 2:
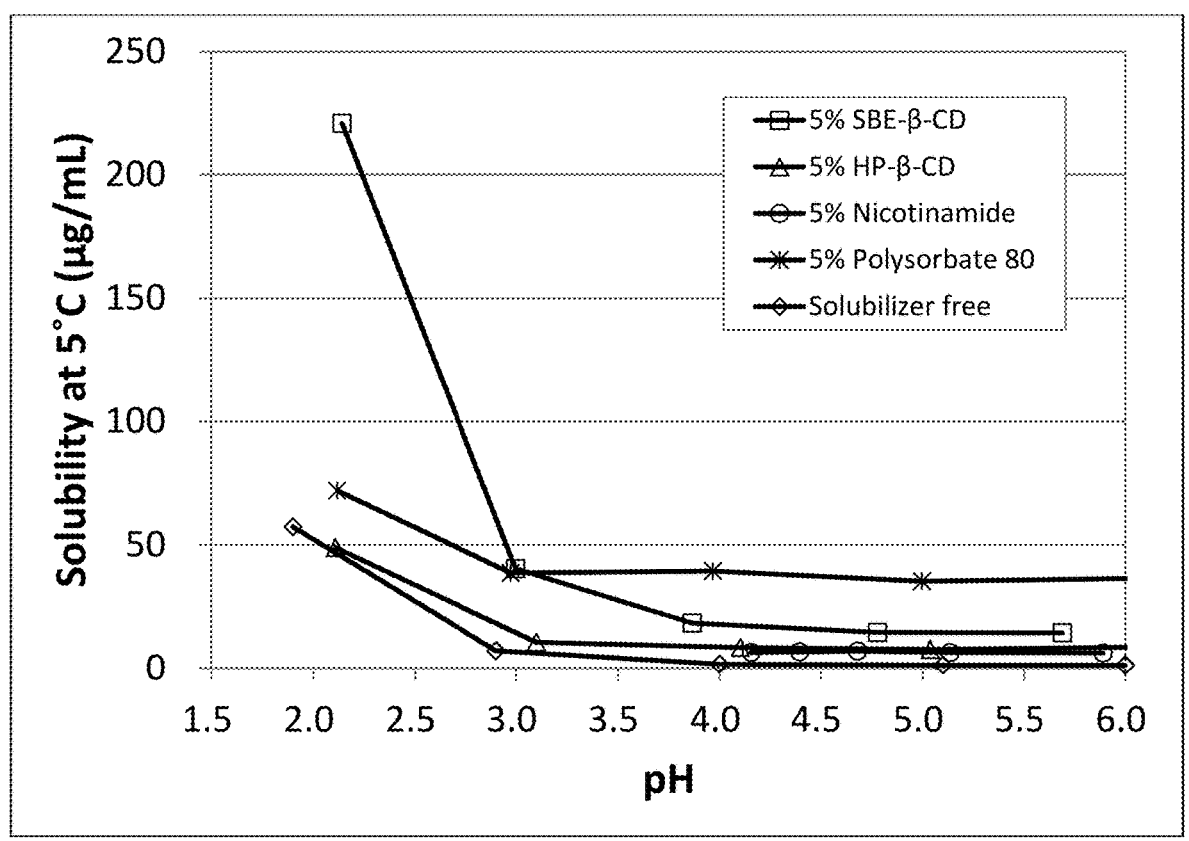
FIG. 2 is a graph illustrating the pH-solubility of perampanel at 5° C. without any solubilizer and with 5% Sulfobutyl Ether Beta Cyclodextrin (SBE-β-CD), 5% Hydroxypropyl Beta Cyclodextrin (HPBCD), 5% nicotinamide, and 5% polysorbate 80.

Perampanel is a basic drug that has poor water solubility. One source of perampanel is FYCOMPA, obtained from Eisai Co. Ltd., of Tokyo. The aqueous solubility at 22° C. decreases from 30 μg/mL at pH 2 to around 1 μg/mL at pH 7. Solubility studies investigated numerous different solubilizers ranging from organic cosolvents, surfactants, amino acids, complexing agents, and cyclodextrins. Further solubility studies were conducted as a function of pH with four selected solubilizers in the pH range 2 to 6. Solubility with all four solubilizers decreased as the pH was increased from 2 to 6. (See FIG. 2)

Studies were conducted to determine the effect of Sulfobutyl Ether Beta Cyclodextrin (SBE-β-CD) concentration and pH on perampanel solubility. In one embodiment, the drug is solubilized at acidic pH in high concentration SBE-β-CD solutions, and then administered at neutral pH in low concentration SBE-β-CD solutions after dilution. The pH range studied for the formulation was 1.5 to 8.0 with a SBE-β-CD concentration range of 20% to 50%. For the diluted administration solution, the pH range studied was 6 to 8 with a SBE-β-CD concentration range of 3% to 9.5%.

Figure 3:
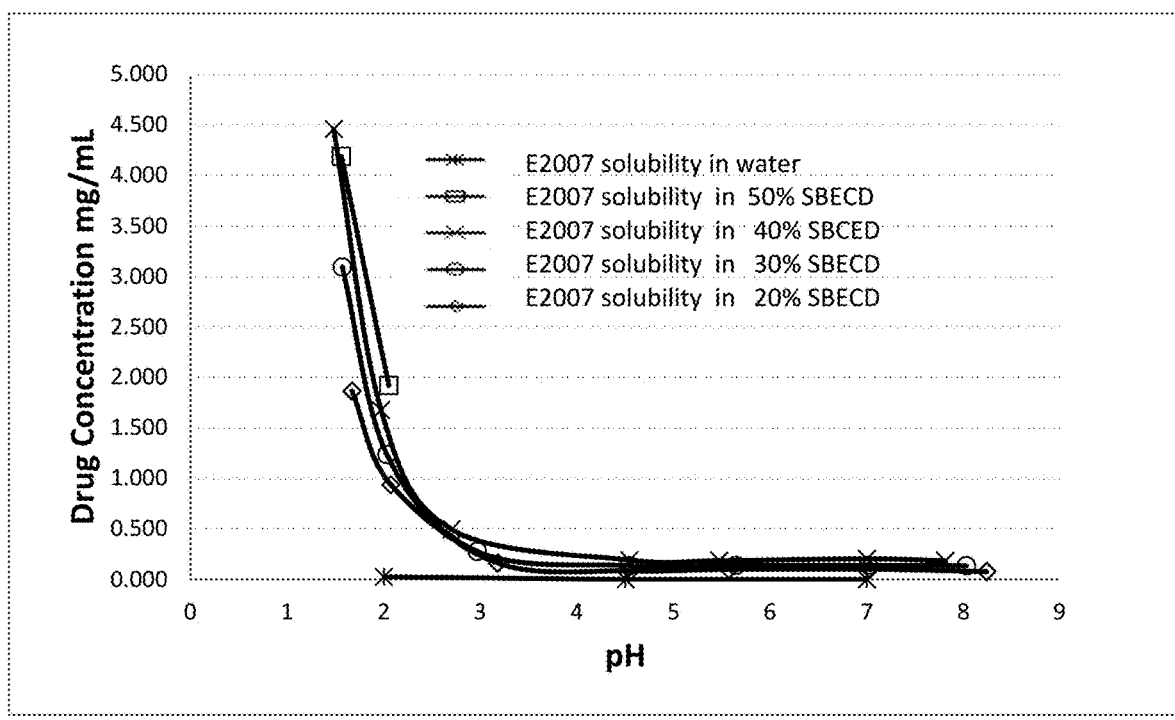
FIG. 3 is a graph illustrating the pH-solubility of perampanel at 22° C. in SBE-βCD solutions varying in concentration from 20% to 50%.

In general, perampanel solubility increased with decreasing pH and increasing SBE-β-CD concentration. FIG. 3 shows solubilization of perampanel in varying SBE-β-CD concentrations.

In one embodiment, the drug product is administered after dilution with an IV fluid. The solubility of perampanel in SBE-β-CD was determined under diluted conditions in the neutral pH range. Perampanel concentrations after dilution can be as low as 0.08 mg/mL (8 mg in 100 mL) and as high as 0.24 mg/mL (12 mg in 50 mL). Table 1 shows that the solubility of perampanel in the dilute SBE-β-CD solutions in the neutral pH range is lower than the expected concentrations of perampanel, indicating that the drug product would be supersaturated at neutral pH.

TABLE 1 pH-Solubility of perampanel in SBE-β-CD concentrations varying from 3% to 9.5%

| Concentration of SBE-β-CD (%) | Solubility of perampanel (mg/mL) | | | |
|---|---|---|---|---|
| | pH 5 | pH 5.5 | pH 7 | pH 8 |
| 3 | NP[a] | 0.02 | 0.03 | 0.03 |
| 6 | NP | 0.04 | 0.03 | 0.06 |
| 9.5 | 0.08 | NP | 0.08 | NP |

[a]Experimental determination Not Performed

Example 2: Studies with Diluted Formulations

Figure 4:
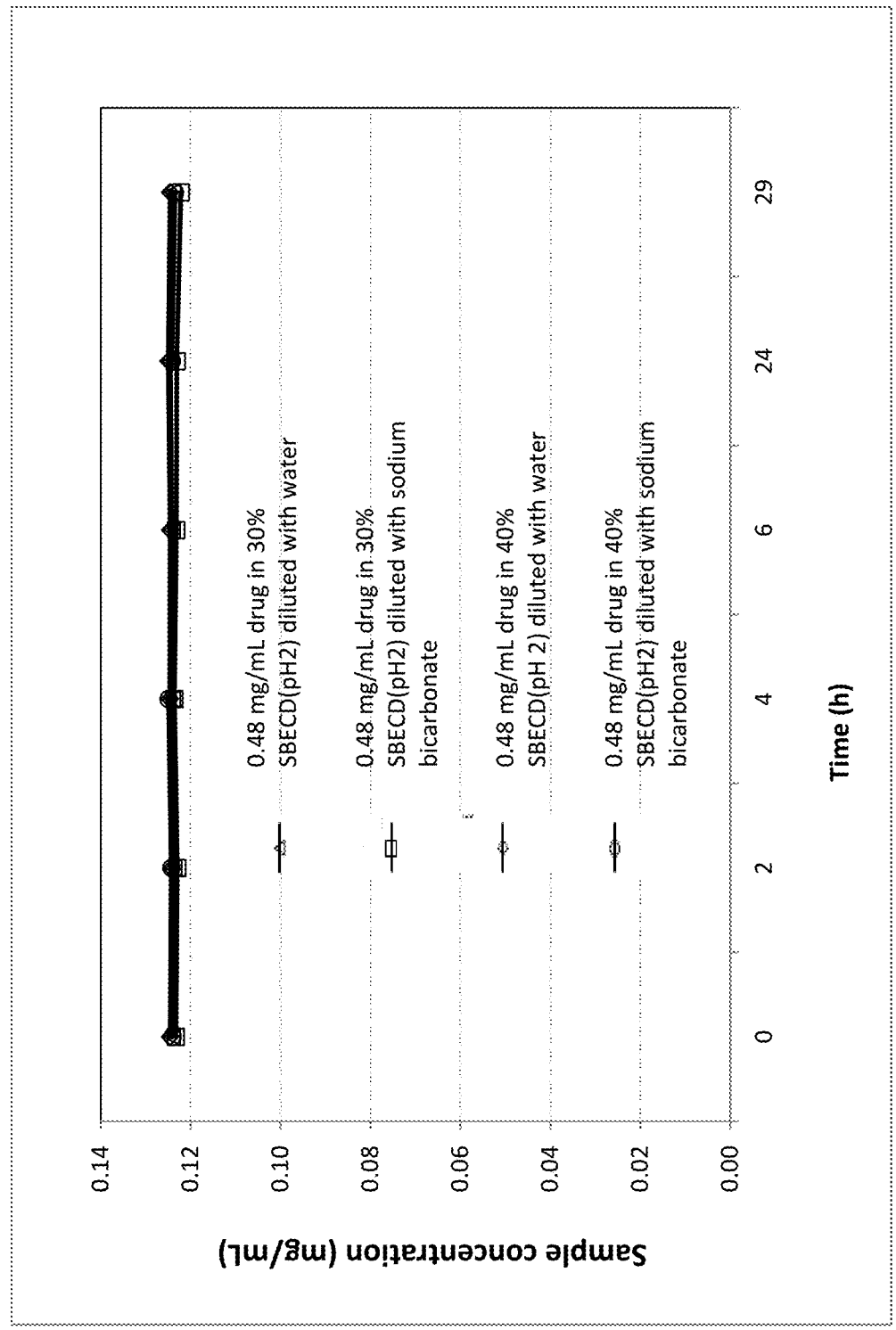
FIG. 4 shows HPLC assay results of 0.48 mg/mL perampanel formulations in 30% and 40% SBE-β-CD after dilution to 0.12 mg/mL in water for injection and 7.5% sodium bicarbonate injection.

Formulations of perampanel (0.48 mg/mL) with 30% and 40% SBE-β-CD at pH 2 were prepared and diluted with either water for injection (WFI) or 7.5% Sodium Bicarbonate Injection. The perampanel concentration in the diluted formulation was 0.12 mg/mL. FIG. 4 shows timed HPLC assay results on the diluted solution over 29 hours storage at room temperature. There was no change in the assay value over this period of time, and no change in the visual clarity of the diluted solution after 5 days, indicating that the solution possesses adequate physical stability for administration.

Figure 5:
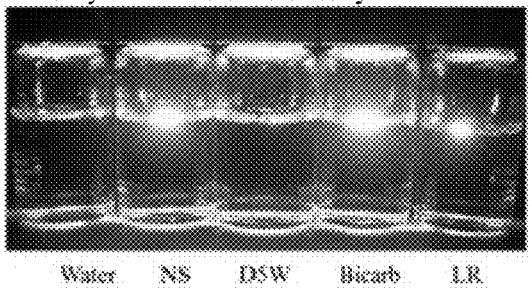
FIG. 5 shows the pH and appearance of a 0.8 mg/mL perampanel formulation in 40% SBE-β-CD after dilution to 0.12 mg/mL in five different diluents.

FIG. 5 shows the pH and appearance of a 0.8 mg/mL perampanel formulation in 40% SBE-β-CD after dilution to 0.12 mg/mL in five different diluents. WFI, D5W, and normal saline were not able to increase the pH of the administered solution to greater than 4. Sodium bicarbonate and Lactated Ringer's were able to increase the pH to 8.63 and 4.74, respectively; however they are not as commonly used in the hospital setting as Saline and D5W. Similar to the results in FIG. 4, the diluted solutions were visually clear when inspected under a Tyndall beam after storage for at least 4 days (see FIG. 5).

These studies with diluted formulations showed that acidic 40% SBE-β-CD solutions of perampanel preclude the use of commonly used diluents such as normal saline and D5W, since these diluents do not have the buffer capacity to increase the pH of the administered solution to acceptable limits. Therefore, an acidic formulation would need to be mixed with a pharmaceutically acceptable diluent to facilitate an increase in pH prior to mixing with saline or D5W.

The studies also showed that diluted formulations of perampanel in SBE-β-CD at neutral pH are stable for several days with no evidence of drug precipitation.

Example 3: Determination of SBE-β-CD to Perampanel Ratio

The general process for making a pH 2 formulation is to solubilize the drug in an acidic SBE-β-CD solution (pH 1.8-2.0), add water for injection (WFI) to make batch volume, and filter through a 0.22 μm filter. The process for making a pH 7 formulation is to solubilize the drug in an acidic SBE-β-CD solution, adjust the pH to 7, add WFI to make batch volume, and filter through a 0.22 μm filter.

Studies were designed to arrive at an acceptable molar ratio of SBE-β-CD to perampanel. Formulation feasibility was assessed by clarity of the solution at pH 2 after overnight mixing of perampanel in the acidic SBE-β-CD solution. Clarity of the solution was also assessed after adjustment to pH 7. As the SBE-β-CD:perampanel ratio is increased, dissolution rate of the drug increases, overall manufacturability is improved, and SBE-β-CD dose to the patient is increased. Formulations having SBE-β-CD:perampanel molar ratios of 28 to 108 were found to be feasible in that they afforded supersaturated solutions at pH 7 that remained clear and precipitate free for at least six hours. A higher ratio allows for increased solubilizing power of SBE-β-CD which increases dissolution rates at pH 2 and better maintains a supersaturated state when the pH is adjusted to 7. A formulation containing SBE-βCD:perampanel ratio of 81 was chosen for further consideration.

There are two formulations that satisfy this SBE-β-CD: perampanel ratio;

(A) 0.8 mg/mL perampanel solution in 40% SBE-β-CD (B) 0.6 mg/mL perampanel solution in 30% SBE-β-CD Both of these formulations are similar in manufacturability, deliver the same SBE-β-CD dose, and are identical with respect to degree of supersaturation after dilution in I.V. fluids at pH 7. A drug product presentation of 4 mg/vial is considered convenient for dosing within the 8 mg to 12 mg range. This presentation is conveniently achieved with a 5 mL fill of a 0.8 mg/mL perampanel solution in a 10 mL vial or a 10 mL fill of a 0.4 mg/mL perampanel solution in 20% SBE-β-CD in a suitably sized vial.

Example 4: Lyophilization Feasibility

The feasibility of lyophilizing solutions of 0.8 to 1.0 mg/mL perampanel in 40% SBE-β-CD at pH 2 and pH 7 was assessed. Lyophilization was done in 10 mL Type 1 glass vials with 4 mg perampanel in each vial. The lyophilized cakes had good structure, and had reconstitution times of 15 to 20 minutes without agitation. The reconstituted solutions at pH 2 and pH 7 were clear and free of particulates. The reconstituted solutions at pH 7 showed good physical stability over time. No drug precipitation was observed in a reconstituted 1 mg/mL formulation at pH 7 even after three months storage at 2-8° C.

It has been shown that drug precipitation in the supersaturated reconstituted solutions at pH 7 can only be brought about through addition of a seed of perampanel which provides a nucleation site and causes drug precipitation over time. During manufacturing, the drug product at pH 7 can be sterile filtered through a 0.22 μm filter which effectively removes any nuclei that can cause precipitation.

Example 5: Formulation Stability

Prototype formulations having a base of 40% SBE-β-CD were manufactured. The formulation pHs were varied at 2.0, 4.5, and 7.0. At pH 2, both liquid and lyophilized formulations having 0.8 mg/mL perampanel were manufactured. At pH 4.5, a lyophilized formulation was manufactured at 0.8 mg/mL. At pH 7, lyophilized formulations were manufactured at 0.8 mg/mL (SBE-β-CD:perampanel ratio=81) and 1.0 mg/ml (SBE-β-CD:perampanel ratio=65), in order to understand the effect of the ratio on physical and chemical stability of perampanel. A description of the components of these five formulations is provided in Table 2.

TABLE 2

Composition of SBE-β-CD based perampanel formulations for stability

| | Amounts per vial[a] | | | | |
|---|---|---|---|---|---|
| Formulation | 0.8 mg/mL pH 2 Liquid | 0.8 mg/mL pH 2 Lyophilized | 0.8 mg/mL pH 4.5 Lyophilized | 0.8 mg/mL pH 7 Lyophilized | 1 mg/mL pH 7 Lyophilized |
| Perampanel | 4 mg | 4 mg | 4 mg | 4 mg | 4 mg |
| SBE-β-CD | 2000 mg | 2000 mg | 2000 mg | 2000 mg | 2000 mg |
| Phosphoric Acid | Adjust to pH 1.8 | Adjust to pH 1.8 | NA | Adjust to pH 1.8 | Adjust to pH 1.8 |
| Tartaric Acid | NA | NA | Adjust to pH 1.8 | NA | Na |
| Sodium Hydroxide | NA | NA | Adjust to pH 4.5 | Adjust to pH 7 | Adjust to pH 7 |
| Water for injection | Q.S. to 5 mL | Q.S. to 5 mL | Q.S. to 5 mL | Q.S. to 5 mL | Q.S. to 4 mL |

[a]An overfill of 0.5 mL was added to each vial (per USP <1151>) to ensure that the withdrawable volume can be removed from the vial.

A stability study was initiated on the prototype formulations listed in Table 2. The formulations were stored at 5° C., 25° C./60% relative humidity (RH), and 40° C./75% RH for 1 month and tested for physical stability (appearance, pH, USP particulates, reconstitution time, appearance of reconstituted solutions) and chemical stability (assay and impurities). A summary of the results of prototype formulation stability is provided below with corresponding data provided.

Appearance:

Liquid: Solution was clear, colorless, and no visible particulates were observed for samples tested up to 1 month.

Lyophilized: No change in cake appearance up to 1 month.

Reconstitution Time:

Reconstitution time for the lyophilized samples tested ranged from 11 minutes to 23 minutes.

Appearance of Reconstituted Solutions:

All reconstituted solutions were clear and colorless. No visible particulates were observed for samples tested up to 1 month. Results are shown in Table 3.

TABLE 3

Reconstitution Time After Storage for One Month

| | Reconstitution Time (minutes) | | | |
|---|---|---|---|---|
| | Zero | 1 Month | | |
| Sample | time | 5° C. | 25° C. | 40° C. |
| 0.8 mg/mL, pH 2, Liquid | NA | NA | NA | NA |
| 0.8 mg/mL, pH 2, Lyophilized | 17 | 15 | 15 | 15 |
| 0.8 mg/mL, pH 4.5, Lyophilized | 11 | 19 | 19 | 19 |
| 1.0 mg/mL, pH 7, Lyophilized | 18 | 16 | 16 | 16 |
| 0.8 mg/mL, pH 7, Lyophilized | 18 | 23 | 23 | 23 | pH:

There was no appreciable change (≤0.2 pH units) in the pH of the formulations up to 1 month. Results are shown in Table 4.

TABLE 4 pH at the initial timepoint and After Storage for One Month

| | pH Results | | | |
|---|---|---|---|---|
| | Zero | 1 Month | | |
| Sample | time | 5° C. | 25° C. | 40° C. |
| 0.8 mg/mL, pH 2, Liquid | 2.0 | 2.1 | 2.1 | 2.1 |
| 0.8 mg/mL, pH 2, Lyophilized | 2.1 | 1.9 | 1.9 | 1.9 |
| 0.8 mg/mL, pH 4.5, Lyophilized | 4.6 | 4.5 | 4.5 | 4.6 |
| 1.0 mg/mL, pH 7, Lyophilized | 7.1 | 7.0 | 7.0 | 7.0 |
| 0.8 mg/mL, pH 7, Lyophilized | 7.0 | 7.0 | 7.0 | 7.0 |

Particulate Matter:

Particulate matter in the formulations at the initial time point was within the USP <788> limits for particles/container. Results are shown in Table 5.

TABLE 5

Particulate Matter in the Formulation

| | Particulate Count (particles/container) | |
|---|---|---|
| Sample | ≥10 μm | ≥25 μm |
| 0.8 mg/mL, pH 2, Liquid | 3 | 0 |
| 0.8 mg/mL, pH 2, Lyophilized | 5 | 0 |
| 0.8 mg/mL, pH 4.5, Lyophilized | 7 | 0 |
| 1.0 mg/mL, pH 7, Lyophilized | 5 | 0 |
| 0.8 mg/mL, pH 7, Lyophilized | 11 | 0 |

≥10 μm: NMT 6000 particles/container
≥25 μm: NMT 600 particles/container

Moisture Content:

The moisture content in the lyophilized formulations ranged from 0.6% to 2.1%. The maximum increase in moisture content after 1 month storage was 1% for the pH 7 lyophilized formulation at 40° C./75% RH. Results are shown in Table 6.

TABLE 6

Moisture Content of Lyophilized Formulation At the Initial Timepoint and After One Month

| | Moisture Content (%) | | | |
|---|---|---|---|---|
| | Zero | 1 Month | | |
| Sample | time | 5° C. | 25° C. | 40° C. |
| 0.8 mg/mL, pH 2, Liquid | NA | NA | NA | NA |
| 0.8 mg/mL, pH 2, Lyophilized | 1.5 | 1.4 | 2.1 | 1.4 |
| 0.8 mg/mL, pH 4.5, Lyophilized | 0.7 | 0.8 | 0.8 | 1.3 |
| 1.0 mg/mL, pH 7, Lyophilized | 0.6 | 0.6 | 0.6 | 0.7 |
| 0.8 mg/mL, pH 7, Lyophilized | 0.8 | 1.6 | 1.2 | 1.8 |

Assay:

There was no appreciable change in assay of the formulations up to 1 month. The maximum loss in potency seen was 1.1% for the pH 2 liquid formulation at 40° C./75% RH. Results are shown in Table 7.

TABLE 7

Potency At Initial Timepoint and After Storage for One Month

| | Perampanel Assay (%) | | | |
|---|---|---|---|---|
| | Zero | 1 Month | | |
| Sample | time | 5° C. | 25° C. | 40° C. |
| 0.8 mg/mL, pH 2, Liquid | 99.5 | 99.3 | 100.9 | 98.4 |
| 0.8 mg/mL, pH 2, Lyophilized | 96.8 | 96.9 | 97.0 | 97.6 |
| 0.8 mg/mL, pH 4.5, Lyophilized | 95.5 | 95.3 | 95.4 | 95.5 |
| 1.0 mg/mL, pH 7, Lyophilized | 96.4 | 96.4 | 96.3 | 96.5 |
| 0.8 mg/mL, pH 7, Lyophilized | 97.3 | 96.7 | 97.0 | 96.6 |

Impurities:

There was no change in the total impurities of the lyophilized formulations (0.06-0.07%) at any of the storage conditions after 1 month. The only increase in impurities seen was with the pH 2 liquid formulation, which went from 0.06% to 0.17% after 1 month storage at 40° C./75% RH. Results of the 1 Month Storage measurement are shown in Table 8.

TABLE 8

Measurement of Impurities at the Initial Timepoint and After Storage for 1 Month

| | Impurities (%) | | | |
|---|---|---|---|---|
| | Zero | 1 Month | | |
| Sample | time | 5° C. | 25° C. | 40° C. |
| 0.8 mg/mL, pH 2, Liquid | 0.06 | 0.06 | 0.07 | 0.17 |
| 0.8 mg/mL, pH 2, Lyophilized | 0.06 | 0.06 | 0.06 | 0.06 |
| 0.8 mg/mL, pH 4.5, Lyophilized | 0.07 | 0.07 | 0.07 | 0.07 |
| 1.0 mg/mL, pH 7, Lyophilized | 0.06 | 0.06 | 0.06 | 0.06 |
| 0.8 mg/mL, pH 7, Lyophilized | 0.06 | 0.06 | 0.06 | 0.06 |

In a separate trial, impurities were measured over a one-year period for lyophilized formulations at 1.0 mg/mL and 0.8 mg/mL. Those results are shown in Table 9A and 9B, and in Table 10A and 10B, respectively.

TABLE 9A

| | | pH 7, Lyophilized, 1 mg/mL, Lot# 692-015 | | | | | | | | | | |
|---|---|---|---|---|---|---|---|---|---|---|---|---|
| | | Zero | 1-Month | | | 3-Month | | | 6-Month | | | 12-Month | |
| Attribute: | | Time | 5° C. | 25° C. | 40° C. | 5° C. | 25° C. | 40° C. | 5° C. | 25° C. | 40° C. | 5° C. | 25° C. |
| Appearance | | White cake | White cake | White cake | White cake | White cake | White cake | White cake | White cake | White cake | White cake | NP | NP |
| Clarity and Completeness of Solution | | Clear C | Clear C | Clear C | Clear C | Clear C | Clear C | Clear C | Clear C | Clear C | Clear C | NP | NP |
| Particulate Matter | 10 μm | 5 | NT | NT | NT | NT | NT | NT | 19 | 19 | 42 | NP | NP |
| (Particles/container) | 25 μm | 0 | NT | NT | NT | NT | NT | NT | 0 | 0 | 0 | NP | NP |
| pH | | 7.1 | 7.0 | 7.0 | 7.0 | 7.1 | 7.1 | 7.1 | 7.1 | 7.0 | 7.1 | 7.0 | 7.0 |
| Water Content (%) | | 0.6 | 0.6 | 0.6 | 0.7 | 0.6 | 0.7 | 0.9 | 0.587 | 0.703 | 0.750 | 0.6 | 0.8 |
| Reconstitution Time (min) | | 18 | 16 | 16 | 16 | 21 | 20 | 20 | 13 | 9 | 11 | NP | NP |
| Assay (HPLC) (%) | | 96.4 | 96.4 | 96.3 | 96.5 | 96.6 | 96.0 | 96.1 | 96.4 | 96.8 | 95.8 | 96.1 | 96.8 |

[1] C: Colorless;

[2] NT: Not Tested;

[3] NA: Not Applicable

TABLE 9B

| | | pH 7, Lyophilized, 1 mg/mL, Lot# 692-015 | | | | | | | | | | |
|---|---|---|---|---|---|---|---|---|---|---|---|---|
| Individual Impurities | Zero | 1-Month | | | 3-Month | | | 6-Month | | | 12-Month | |
| RRT | Time | 5° C. | 25° C. | 40° C. | 5° C. | 25° C. | 40° C. | 5° C. | 25° C. | 40° C. | 5° C. | 25° C. |
| 1.46 | 0.02 | 0.02 | 0.02 | 0.03 | 0.02 | 0.02 | 0.02 | 0.02 | 0.02 | 0.03 | 0.02 | 0.02 |
| 1.86 | 0.01 | 0.01 | 0.01 | 0.01 | 0.01 | 0.01 | 0.01 | 0.01 | 0.01 | 0.01 | 0.01 | 0.01 |
| 1.98 | 0.01 | 0.01 | 0.01 | 0.01 | 0.01 | 0.01 | 0.01 | 0.01 | 0.01 | <0.01 | 0.01 | 0.01 |
| 2.01 | ND | ND | ND | ND | <0.01 | <0.01 | <0.01 | ND | ND | ND | <0.01 | <0.01 |
| 2.13 | 0.01 | 0.01 | 0.01 | 0.01 | 0.01 | 0.01 | 0.01 | 0.01 | 0.01 | 0.01 | 0.01 | <0.01 |
| 2.23 | 0.01 | 0.01 | 0.01 | 0.01 | 0.01 | 0.01 | 0.01 | 0.01 | 0.01 | 0.01 | <0.01 | <0.01 |

TABLE 10A

| | | 1-Month | | | 3-Month | | | 6-Month | | | 12-Month | |
|---|---|---|---|---|---|---|---|---|---|---|---|---|
| Attribute: | Zero Time | 5° C. | 25° C. | 40° C. | 5° C. | 25° C. | 40° C. | 5° C. | 25° C. | 40° C. | 5° C. | 25° C. |
| Appearance | White cake | White cake | White cake | White cake | White cake | White cake | White cake | White cake | White cake | White cake | NP | NP |
| Clarity and Completeness of Solution | Clear C | Clear C | Clear C | Clear C | Clear C | Clear C | Clear C | Clear C | Clear C | Clear C | NP | NP |
| Particulate Matter 10 μm | 11 | NT | NT | NT | NT | NT | NT | 59 | 22 | 13 | NP | NP |
| (Particles/Container) 25 μm | 0 | NT | NT | NT | NT | NT | NT | 0 | 0 | 0 | NP | NP |
| pH | 7.0 | 7.0 | 7.0 | 7.0 | 7.0 | 7.0 | 7.0 | 7.0 | 7.0 | 7.0 | 7.0 | 7.0 |
| Water Content (%) | 0.8 | 1.6 | 1.2 | 1.8 | 1.7 | 1.7 | 2.0 | 0.904 | 1.557 | 1.057 | 1.6 | 0.9 |
| Reconstitution Time | 18 | 23 | 23 | 23 | 14 | 20 | 20 | 14 | 15 | 15 | NP | NP |
| Assay (HPLC) (%) | 97.3 | 96.7 | 97.0 | 96.6 | 97.3 | 96.8 | 97.1 | 96.8 | 96.8 | 96.8 | 96.9 | 97.3 | pH 7, Lyophilized, 0.8 mg/mL, Lot# 692-009

[1] C: Colorless;
[2] NT: Not Tested;
[3] NA: Not Applicable

TABLE 10B pH 7, Lyophilized, 0.8 mg/mL, Lot# 692-009

| Individual Impurities | Zero | 1-Month | | | 3-Month | | | 6-Month | | | 12-Month | |
|---|---|---|---|---|---|---|---|---|---|---|---|---|
| RRT | Time | 5° C. | 25° C. | 40° C. | 5° C. | 25° C. | 40° C. | 5° C. | 25° C. | 40° C. | 5° C. | 25° C. |
| 1.46 | 0.02 | 0.02 | 0.02 | 0.02 | 0.02 | 0.02 | 0.02 | 0.02 | 0.02 | 0.03 | 0.02 | 0.02 |
| 1.86 | 0.01 | 0.01 | 0.01 | 0.01 | 0.01 | 0.01 | 0.01 | 0.01 | 0.01 | 0.01 | 0.02 | 0.01 |
| 1.98 | 0.01 | 0.01 | 0.01 | 0.01 | 0.01 | 0.01 | 0.01 | 0.01 | 0.01 | 0.01 | 0.01 | 0.01 |
| 2.01 | ND | ND | ND | ND | <0.01 | <0.01 | <0.01 | ND | ND | ND | <0.01 | <0.01 |
| 2.13 | 0.01 | 0.01 | 0.01 | 0.01 | <0.01 | 0.01 | 0.01 | 0.01 | 0.01 | 0.01 | 0.01 | 0.01 |
| 2.23 | 0.01 | 0.01 | 0.01 | 0.01 | 0.01 | 0.01 | 0.01 | 0.01 | 0.01 | 0.01 | <0.01 | <0.01 |

[1] ND: Not detected

Example 6: Drug Product Stability During Administration

In one embodiment, the lyophilized drug product will undergo reconstitution, dilution into an I.V. fluid bag, and passage through an infusion set and catheter system.

Reconstituted solutions at pH 7 remained visually clear and precipitate free (under Tyndall beam) for up to three months at 2-8° C. Studies were undertaken to test whether any precipitation could be detected using analytical particulate testing methods. The physical stability of the reconstituted solution was determined as a function of time on a 1 mg/mL perampanel formulation at pH 7 using the USP <788> test and light scattering intensity measurements. The USP <788> test detects particulate matter in the micron size range. Light scattering intensity can be used as an early indication of an increase in sub-visible particles that could potentially be precursors to drug precipitation. The results in Table 11 show no change in particulate matter or light scattering intensity in the reconstituted solution up to 72 hours after reconstitution. This result confirms that no precipitation occurs in the reconstituted solution even at the sub-visible particulate level.

TABLE 11

Physical stability of a 1 mg/mL perampanel lyophilized formulation at pH 7 after reconstitution

| Time elapsed after reconstitution (h) | HIAC Testing[a] (Particles/container) | | | | Light Scattering Intensity (KHz) |
|---|---|---|---|---|---|
| | ≥2 μm | ≥5 μm | ≥10 μm | ≥25 μm | |
| 0 | 946 | 133 | 15 | 0 | 100 |
| 24 | 1297 | 295 | 45 | 1 | 100 |
| 48 | 564 | 120 | 20 | 1 | 95 |
| 72 | 465 | 121 | 25 | 1 | 95 |

[a]USP <788> requirements are:
≥10 μm—NMT 6000 particles/container
≥25 μm—NMT 600 particles/container

Example 7: Compatibility Studies

During administration, the reconstituted drug product may be pulled into a syringe prior to mixing with an I.V. fluid. Therefore, the physical stability and compatibility of the reconstituted drug product with polypropylene (PE) syringes was assessed. The formulation was kept in contact with the syringe at room temperature for 24 hours along with a control solution held in a glass vial. Table 12 shows that there was no difference in the perampanel assay between the syringe and control sample, indicating that the drug product is physically stable and compatible when in contact with the syringe for up to 24 hours.

TABLE 12

Compatibility of perampanel formulation (pH 7 lyophilized) with polypropylene syringe. Concentrations and appearance shown are after 24 h storage at room temperature.

| Sample | Perampanel Concentration (mg/mL) | Appearance of solution |
|---|---|---|
| Control | 0.70 | Visually clear |
| Syringe | 0.70 | Visually clear |

The physical stability and compatibility of the pH 7 lyophilized formulation was assessed in normal saline taken in a polyethylene (PE) copolymer I.V. bag. The perampanel concentrations studied were 0.08 mg/mL and 0.24 mg/mL. Samples were removed from the bag at various time points for up to 72 hours, and analyzed for assay, pH, and non-visible particulates. The solutions appeared clear and showed no change in pH, light scattering intensity, and assay after 72 hours in normal saline held in the PE bag (Table 13). These data conclude that there is no physical instability or incompatibility exhibited by perampanel in the I.V. bags made of PE for up to 72 hours.

TABLE 13

Compatibility of perampanel formulation in normal saline taken in a polyethylene (PE) copolymer bag. pH, light scattering, and perampanel assay were measured over 72 hours.

| Target Perampanel Conc. (mg/mL) | Time (h) | Light Scattering Intensity (KHz) | pH | Assay (mg/mL) |
|---|---|---|---|---|
| 0.08 | 0 | 58-66 | 7.3 | 0.071 |
|  | 24 | 56-64 | 7.3 | 0.070 |
|  | 48 | 50-56 | 7.3 | 0.070 |
|  | 72 | 50-56 | 7.3 | 0.070 |
| 0.24 | 0 | 85-91 | 7.2 | 0.232 |
|  | 24 | 72-82 | 7.3 | 0.230 |
|  | 48 | 68-75 | 7.3 | 0.229 |
|  | 72 | 68-78 | 7.3 | 0.227 |

Compatibility studies were also repeated after dilution of perampanel formulation with 5% Dextrose taken in a polyethylene (PE) copolymer I.V. bag. Samples were removed from the bag at various time points up to 76 hours, and analyzed by HPLC. Table 14 shows no loss in perampanel concentration over 76 hours.

TABLE 14

Compatibility of perampanel formulation in 5% Dextrose taken in a polyethylene (PE) copolymer bag. Perampanel assay was measured over 72 hours.

| Target Perampanel Conc. (mg/mL) | Time (h) | Assay (mg/mL) |
|---|---|---|
| 0.12 | 0 | 0.125 |
|  | 6 | 0.124 |
|  | 24 | 0.123 |
|  | 30 | 0.125 |
|  | 52 | 0.124 |
|  | 76 | 0.123 |

The physical stability and compatibility of the pH 7 lyophilized formulation was also assessed in normal saline in a polyvinylchloride (PVC) I.V. bag. The perampanel concentration studied was 0.12 mg/mL. Samples were removed from the bag at various time points for up to 11 hours, and assayed for perampanel. Table 15 shows that the PVC bag showed adsorptive losses of approximately 18% over 11 hours.

TABLE 15

Compatibility of perampanel formulation in Normal Saline in a polyvinyl chloride (PVC) bag. Perampanel assay was measured over 11 hours.

| Target Perampanel Conc. (mg/mL) | Time (h) | Assay (mg/mL) |
|---|---|---|
| 0.12 | 0 | 0.124 |
|  | 1 | 0.119 |
|  | 2 | 0.117 |
|  | 4 | 0.112 |
|  | 6 | 0.108 |
|  | 8 | 0.106 |
|  | 11 | 0.102 |

The compatibility of the drug product with infusion set and catheter system were studied. Two administration sets were evaluated; one set containing polyethylene coated tubing, and one set containing polyvinyl chloride tubing. These administration sets were evaluated with perampanel in normal saline.

The infusion set was connected to the normal saline bag on one end and to the I.V. catheter on the other end. The diluted drug product was kept in contact with all components for 72 hours. At various time points, 25 mL of the solution was collected from the catheter and analyzed for perampanel assay. The solution in contact with the PVC administration set showed a 42% loss in drug potency within the first 2 hours. The appearance of the sub-potent solution was clear and free of precipitate; therefore the potency loss is attributed to adsorption of the drug to the PVC tubing. The solution in contact with the polyethylene coated administration set showed no drug loss over 72 hours. Additionally, there was no change in the pH and light scattering intensity measurements of the solution in contact with the PE administration set.

Example 8 Induction Time Study

Figure 6:
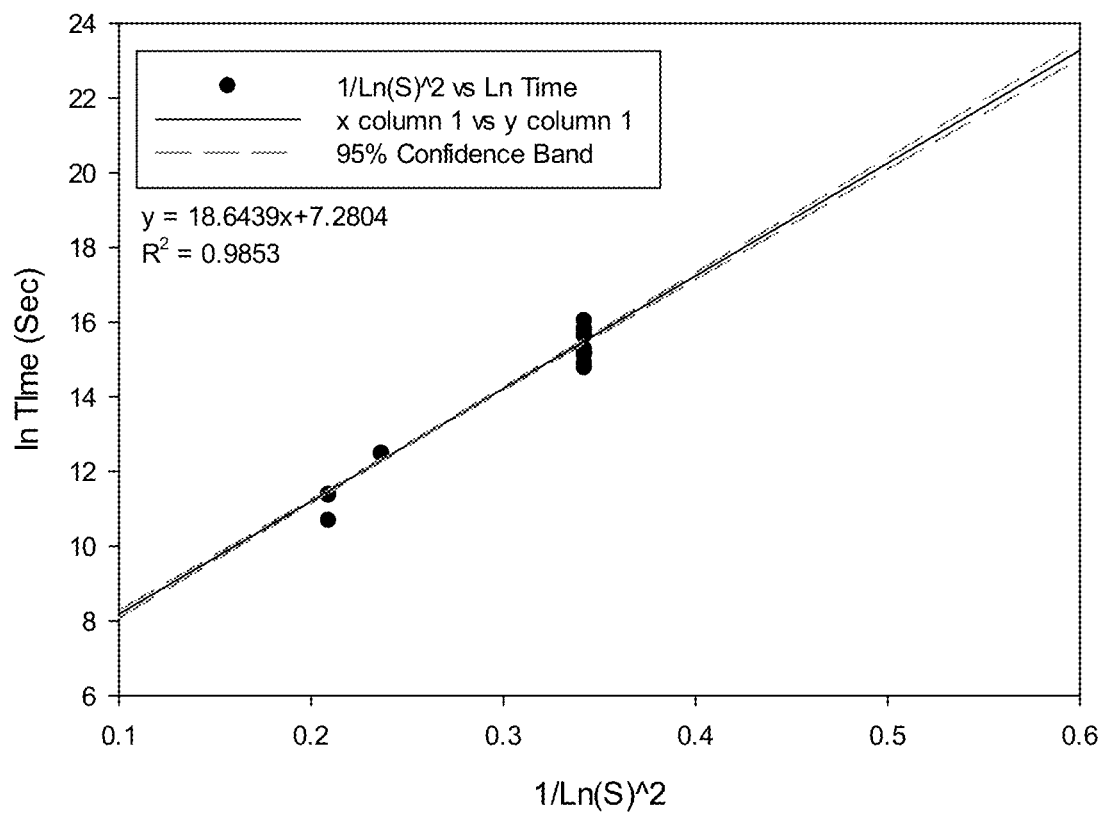
FIG. 6 shows measured and predicted induction times for various concentrations of perampanel at 40% SBE-β-CD at room temperature and in 5 mL of volume.

Induction time studies were performed to determine the period of time that would elapse before crystal formation for various concentrations of perampanel at 40% SBE-β-CD, pH 7 at room temperature and in 5 mL of volume. The concentrations of the studied solutions measured were 1.16, 1.64, and 1.97 (mg/mL). The precipitation time data was analyzed as per the method used in Zaitseva et. al. in J. Crystal Growth, 148 (1995) 276-282. From these data, the induction time of a 0.8 mg/mL solution (which is equivalent to x=0.599 on the In Time (sec) vs $1/Ln(S)^2$ graph) was predicted to be 3.3 years (95% Confidence Intervals were 1.3 years on the low end and 7.9 years on the high end). The data analysis used to make this prediction is provided in FIG. 6, where S corresponds to the degree of supersaturation and S=X/Xo, where Xo is the solubility. Since the reconstituted vial of Drug Product only needs to remain particulate free for up to a few days, the predicted induction times support the viability of the 40% SBE-β-CD, pH 7 formulation.

Example 9 Metastable Zone Width Studies

Meta-Stable Zone Width studies on SBE-β-CD based perampanel formulations containing varying concentrations of perampanel were performed to estimate the meta-stable zone for formulations containing 40% SBE-β-CD at pH 7. Lyophilization provides for long-term storage but requires reconstitution prior to use. When the lyophilized formulation is reconstituted, the solution is in a meta-stable supersaturated state. Meta-stable zone width analysis provides an estimate of how close a formulation is to the meta-stable state boundary.

Perampanel solutions of varying concentration were prepared in 40% SBE-β-CD at pH 7 and placed in a warm temperature controlled mixing vessel with a LASENTECH® probe to detect precipitation. Although those skilled in the art will recognize that formulations as stated in the prior examples may be prepared by a number of methods, the following method is used to prepare formulations at various perampanel concentrations in 40% SBE-β-CD, pH 7, liquid form, for the trials below. First, a SBE-β-CD solution at pH 1.8 is prepared by adding about 25 ml of water to a beaker, then adding about 20 g of SBE-β-CD. The SBE-β-CD has a water content of 4.7%, is 100% pure, and has a theoretical weight of 20 g/0.953, or 21.0 g. The SBE-β-CD is slowly added with mixing until it has dissolved. The volume is checked to ensure that it is not greater than 40 ml. pH of the solution is adjusted to pH 1.75 with 85% phosphoric acid.

The weight of perampanel used to prepared the desired concentration is then calculated by dividing 100 mg by the product of (1-[moisture content of perampanel/100]) and (anhydrous purity of perampanel/100). In some examples the moisture content is 3.7% and the anhydrous purity is 99.9%. The calculated amount of perampanel is added to the pH 1.75 solution, then mixed overnight at 40° C. The solution is filtered through a 20 μm filter at 40° C., then warmed to 40° C. At that temperature pH is adjusted to 7. Volume is adjusted to 50 mL with water and mixed.

The solutions were cooled at defined rates and the temperature at which precipitation occurred was recorded. The potency for each sample was measured by HPLC analysis. The precipitation temperature data were analyzed as per the method described by Sangwal, K. in *Crystal Growth and Design*, 9, 2 (2009) 942-950.

Figure 7:
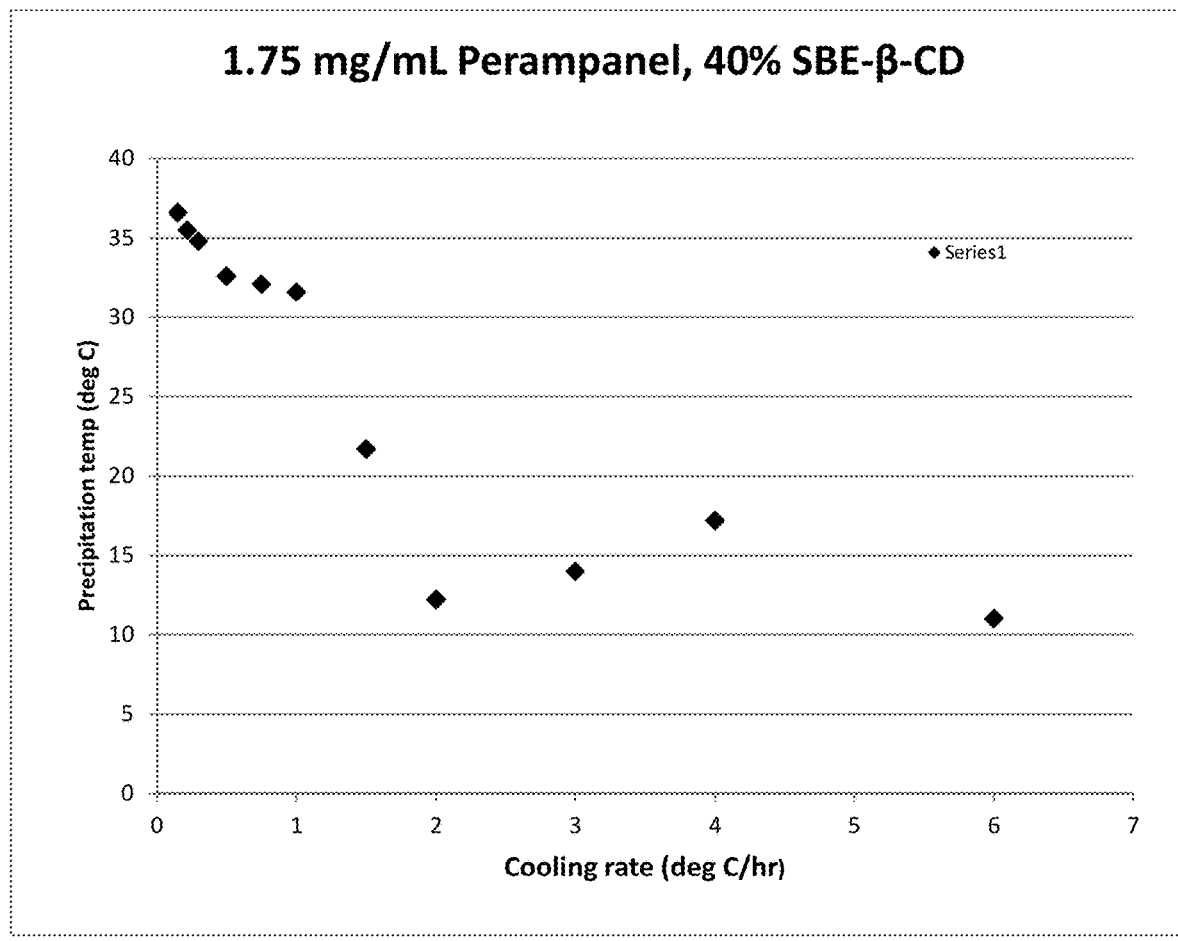
FIG. 7 shows precipitation temperature as a function of cooling rate for a 1.75 mg/mL solution, 40% SBE-β-CD, showing that linear extrapolation to zero cooling rate should be performed with data from experiments performed at <0.5 degrees/hr.

Analysis of initially collected data indicated that the best method to extrapolate the meta-stable zone boundary is to perform a linear extrapolation to zero cooling rate on data collected from cooling rates of less than or equal to 0.5 deg/hr, as shown in FIG. 7. The initially collected data is summarized in Table 15.

TABLE 15

Summary of Meta-stable Zone Width Study Data.

| Experiment # | Cooling Rage (deg C./hour) | Ppt T (deg C.) | Measured Conc. perampanel (mg/mL) |
| --- | --- | --- | --- |
| MC2-102-184 | 0.25 | NP | 1.05 |
| MC2-102-185 | 0.40 | 17.4 | 1.30 |
| MC2-102-179 | 0.60 | NP | 1.05 |
| MC2-102-176 | 0.75 | NP | 0.98 |
| MC2-102-181 | 0.10 | 33.5 | 1.46 |
| MC2-102-172 | 0.15 | 33.3 | 1.53 |
| MC2-102-178 | 0.22 | 33.7 | 1.42 |
| MC2-102-170 | 0.30 | 29.6 | 1.43 |
| MC2-102-174 | 0.40 | 30.9 | 1.51 |
| MC2-102-169 | 0.50 | 29.5 | 1.43 |
| MC2-102-163 | 0.75 | 20.3 | 1.51 |
| MC2-102-168 | 1.00 | 9.5 | 1.52 |
| MC2-102-159 | 2.00 | 6.4 | 1.39 |
| MC2-102-164 | 0.15 | 36.6 | 1.74 |
| MC2-102-182 | 0.22 | 35.5 | 1.77 |
| MC2-102-165 | 0.30 | 34.8 | 1.80 |
| MC2-102-161 | 0.50 | 32.6 | 1.79 |
| MC2-102-166 | 0.75 | 32.1 | 1.78 |
| MC2-102-149 | 1.00 | 31.6 | 1.64 |
| MC2-102-162 | 1.50 | 21.7 | 1.74 |

TABLE 15-continued

Summary of Meta-stable Zone Width Study Data.

| Experiment # | Cooling Rage (deg C./hour) | Ppt T (deg C.) | Measured Conc. perampanel (mg/mL) |
| --- | --- | --- | --- |
| MC2-102-155 | 2.00 | 12.2 | 1.68 |
| MC2-102-150 | 3.00 | 13.7 | 1.69 |
| MC2-102-157 | 4.00 | 17.2 | 1.70 |
| MC2-102-151 | 6.00 | 11.3 | 1.63 |
| MC2-102-154 | 1.00 | 30.5 | 1.97 |
| MC2-102-148 | 3.00 | 21.6 | 1.99 |
| MC2-102-153 | 6.00 | 12.6 | 1.81 |
| MC2-102-187 | 0.30 | 10.2 | 1.10 |
| MC2-102-192 | 0.20 | 22.9 | 1.21 |
| MC2-102-193 | 0.10 | 24.1 | 1.26 |
| MC2-102-197 | 0.40 | 2.6 | 1.06 |
| MC2-1108-001 | 0.40 | 12.8 | 0.97 |

NP = No Precipitation observed.

Figure 8:
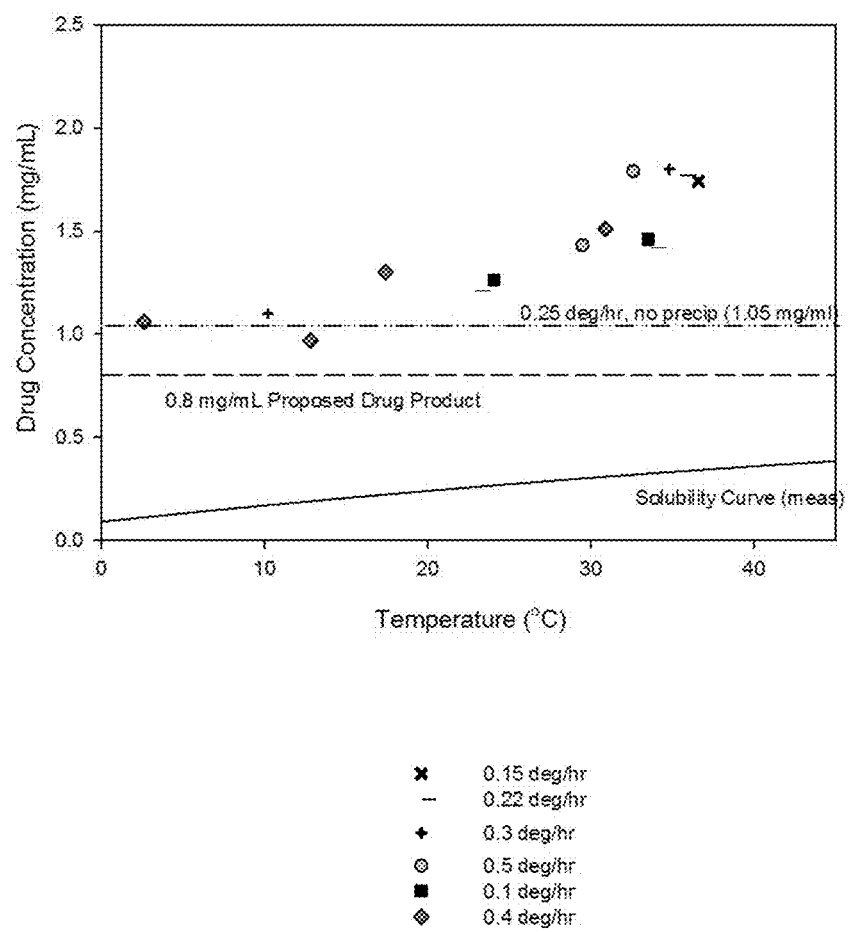
FIG. 8 shows precipitation temperatures of a samples from a 40% SBE-β-CD, pH7 solution as a function of drug concentration and cooling rate.
Figure 9:
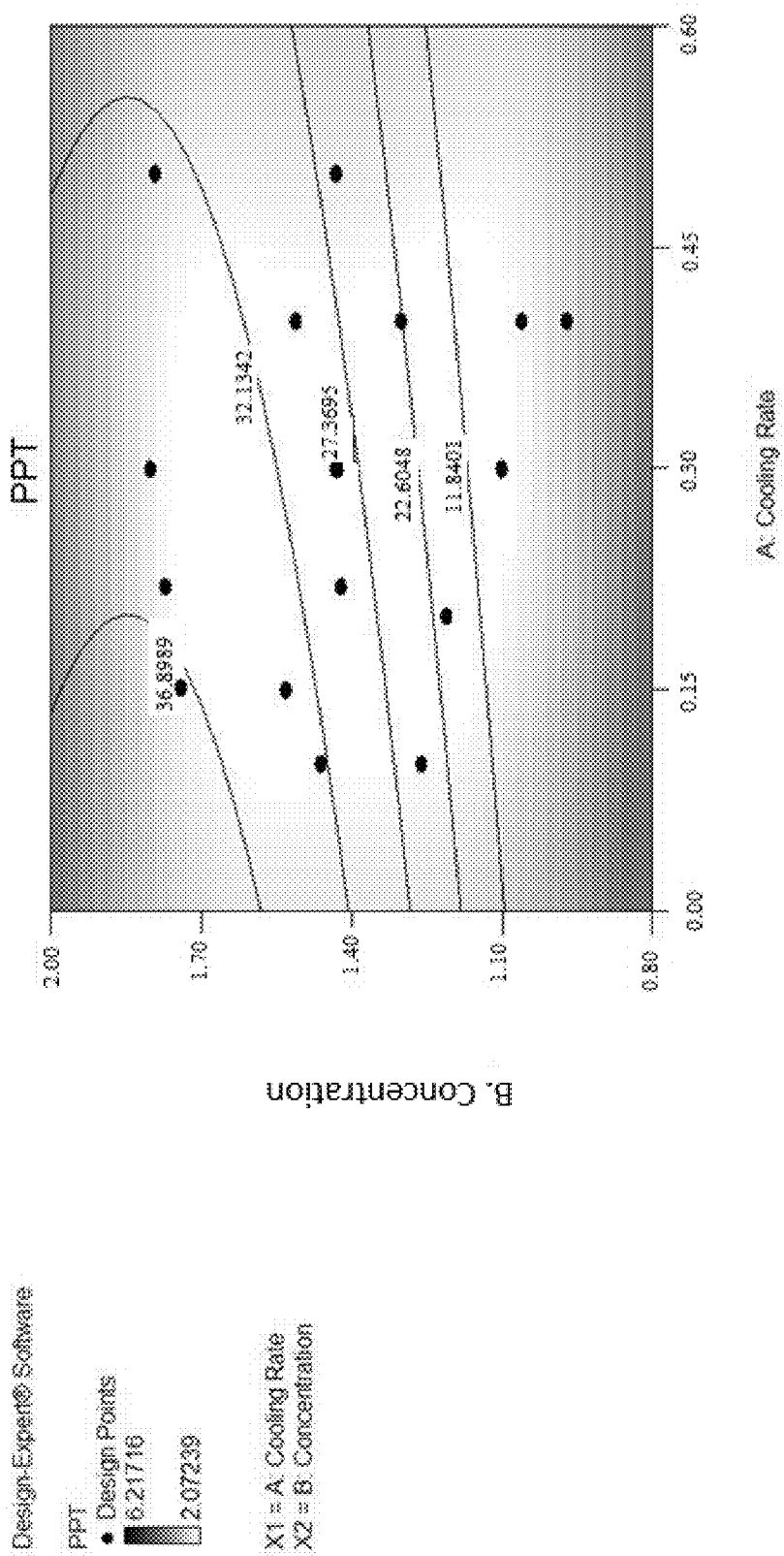
FIG. 9 shows a contour plot of precipitation temperature (Deg C.) as a function of concentration (mg/mL) and cooling rate (Deg C./hr) showing the individual data points and the fit of the data as contour lines.
Figure 10:
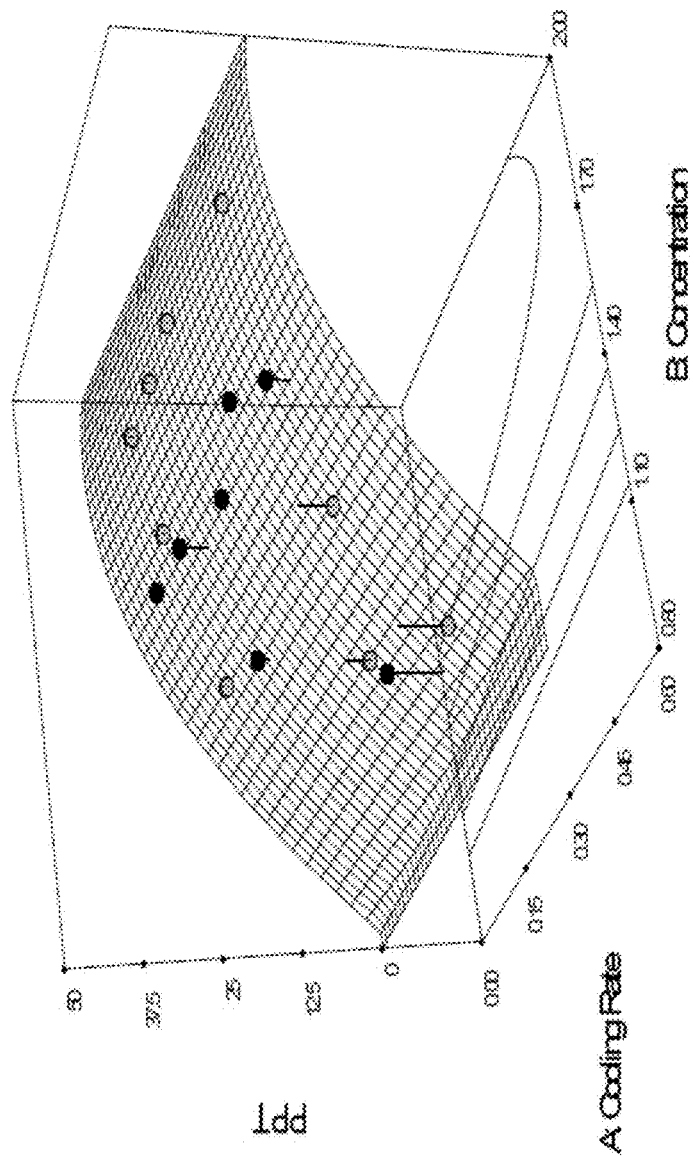
FIG. 10 is a 3-D plot illustrating the relationship between cooling rate (deg/hr), perampanel concentration (mg/mL) and precipitation temperature (Deg C.). This plot is another representation of the same data provided in FIG. 9. The precipitation temperature at zero cooling rate is extrapolated from these data to provide the metastable zone boundary.

A plot of the precipitation temperature of perampanel from a 40% SBE-β-CD, pH 7 solution as a function of drug concentration (mg/mL) and cooling rate (deg C./hr) is provided in FIG. 8. A contour plot (see FIG. 9) and a 3-D plot (see FIG. 10) illustrating the relationship between cooling rate (deg/hr), perampanel concentration (mg/mL) and precipitation temperature were generated using the DESIGN-EXPERT® software, version 7.1.6. The DESIGN-EXPERT® model used the precipitation temperature, cooling rate, concentration and concentration terms to fit a surface to the data. The DESIGN-EXPERT® program was then able to extrapolate the precipitation temperature at zero cooling rate for different drug concentrations with 95% confidence intervals from the fit of the data.

This extrapolated data was used to prepare FIG. 11, which predicts the meta-stable zone boundary for perampanel in a 40% SBE-β-CD formulation at pH 7. Theoretically, if the drug concentration remains at or below the meta-stable zone boundary, then the drug should not precipitate from solution at the defined temperatures. These data indicate that 0.8 mg/mL should not precipitate during storage at temperatures down to zero degrees C.; however, due to the variability of the results, the 95% confidence interval is large at the lower drug concentrations.

The results from this study indicate that the 0.8 mg/mL formulation is within the meta-stable zone down to zero degrees C. Due to the variability in the data (especially at lower drug concentrations), the lower 95% confidence interval of the meta-stable zone crosses zero degrees Celsius at around 10 degrees Celsius. Therefore, it is recommended that after reconstitution, the solution be stored at controlled room temperature and have a restriction against refrigerated and frozen storage to insure that the drug product remains within the meta-stable zone and precipitation does not occur.

Example 10

A formulation of perampanel as disclosed herein is administered intravenously to a patient in need of such treatment. Treatment is repeated as needed and deemed appropriate by a treating physician.

While particular embodiments have been described and illustrated, it should be understood that these are not limiting in any way, since modifications may be made by persons of skill in the art. The present application contemplates any and all modifications that fall within the spirit and scope of the aqueous based pharmaceutical formulations of 1,2-dihydropyridine compounds as disclosed and claimed herein.

Numbered Embodiments

1. A pharmaceutical formulation comprising a solubilizing agent and a therapeutically effective amount of a compound or a hydrate of a compound represented by the following formula,

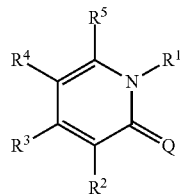

wherein Q indicates O, $R^3$ and $R^5$ are the same as or different from each other and each indicates a hydrogen atom or a $C_{1-6}$ alkyl group; and $R^1$ indicates $C_{3-8}$ cycloalkyl group, a 5 to 14 membered aromatic heterocyclic group, a $C_{6-14}$ aromatic hydrocarbocyclic group, or a 5 to 14 membered aromatic heterocyclic group, which may be substituted, respectively, and $R^2$ and $R^4$ are the same as or different from each other and each indicates a group represented by the formula —X-A wherein X indicates a single bond and A indicates a $C_{3-6}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively;
wherein said compound and said solubility agent are present in a ratio whereby dilution of said formulation in aqueous medium provides the compound in supersaturated aqueous solution.
2. The pharmaceutical formulation of claim 1, wherein the compound and the solubilizing agent are present in a molar ratio of between 60 to 110 moles solubilizing agent to moles compound.
3. The pharmaceutical formulation of claim 1, wherein said solubilizing agent is a cyclodextrin.
4. The pharmaceutical formulation of claim 3, wherein said solubilizing agent is selected from the group consisting of α-cyclodextrin, β-cyclodextrin, hydroxypropyl β-cyclodextrin and a mixture of two or more different cyclodextrins.
5. The pharmaceutical formulation of claim 4, wherein said solubilizing agent is a sulfobutyl ether β-cyclodextrin.
6. The pharmaceutical formulation of claim 5, wherein said solubilizing agent is sulfobutyl ether β-cyclodextrin sodium.
7. The pharmaceutical formulation of claim 5, wherein said compound is perampanel or a hydrate thereof.
8. The pharmaceutical formulation of claim 7, wherein the sulfobutyl ether β-cyclodextrin to perampanel molar ratio is between 28 and 108.
9. The pharmaceutical formulation of claim 1, wherein the compound is in the amorphous phase.
10. The pharmaceutical formulation of claim 1, wherein the formulation is in solution.
11. The pharmaceutical formulation of claim 10, wherein said solution is an aqueous solution.
12. The pharmaceutical formulation of claim 9, wherein the formulation is lyophilized.
13. A storage-stable aqueous pharmaceutical formulation for intravenous administration comprising an aqueous, supersaturated perampanel solution and sulfobutyl ether β-cyclodextrin.
14. The pharmaceutical formulation of claim 13, wherein said perampanel and said sulfobutyl ether β-cyclodextrin are present in a molar ratio of moles sulfobutyl ether β-cyclodextrin to moles perampanel of between 60 and 110.
15. The pharmaceutical formulation of claim 14, wherein said aqueous, supersaturated perampanel solution has a pH between 2.5 and 9.
16. The pharmaceutical formulation of claim 15, wherein said aqueous supersaturated perampanel solution has a pH between 6 and 8.
17. The pharmaceutical formulation of claim 13, wherein the amount of solubilizing agent, by weight, is between 0.005% and 60%.
18. The pharmaceutical formulation of claim 13, wherein the amount of solubilizing agent, by weight, is between 3% and 9.5%.
19. The pharmaceutical formulation of claim 13, wherein the pharmaceutical formulation is at a temperature greater than or equal to 0° C.
20. The pharmaceutical formulation of claim 13, wherein the pharmaceutical formulation is at a temperature greater than or equal to 10° C.
21. A process for preparing a pharmaceutical formulation in an aqueous medium comprising a solubilizing agent and a therapeutically effective amount of a compound represented by the following formula,

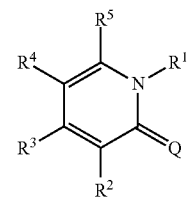

wherein Q indicates O, $R^3$ and $R^5$ are the same as or different from each other and each indicates a hydrogen atom or a $C_{1-6}$ alkyl group; and $R^1$ indicates a $C_{3-8}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, and $R^2$ and $R^4$ are the same as or different from each other and each indicates a group represented by the formula —X-A wherein X indicates a single bond and A indicates a $C_{3-6}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, comprising the steps of
a) solubilizing the compound at acidic pH in a solubilizing agent, and
b) adjusting the pH to between 6 and 8 with the addition of a diluent.
22. The process of claim 21, wherein said solubilizing agent is selected from the group consisting of α-cyclodextrin, β-cyclodextrin, and hydroxypropyl β-cyclodextrin.

23. The process of claim 21, wherein said solubilizing agent is sulfobutyl ether β-cyclodextrin sodium.
24. The process of claim 23, wherein said compound is perampanel or a hydrate thereof.
25. The process of claim 23, further comprising lyophilizing said pharmaceutical formulation.
26. The process of claim 25, wherein said lyophilization step occurs at a concentration of compound lower than a concentration of compound at which it is supersaturated in the aqueous medium.
27. A method of treating a neurodegenerative disease with a pharmaceutical formulation in an aqueous medium comprising a solubilizing agent and a therapeutically effective amount of a compound represented by the following formula or a hydrate thereof,

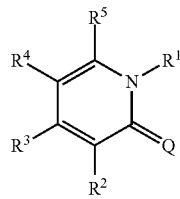

wherein Q indicates O, R³ and R⁵ are the same as or different from each other and each indicates a hydrogen atom or a $C_{1-6}$ alkyl group; and R¹ indicates a $C_{3-8}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, and R² and R⁴ are the same as or different from each other and each indicates a group represented by the formula —X-A wherein X indicates a single bond and A indicates a $C_{3-6}$ cycloalkyl group, a 5 to 14 membered non-aromatic heterocyclic group, a $C_{6-14}$ aromatic hydrocarbocyclic group, or a 5 to 14 membered aromatic heterocyclic group, which may be substituted, respectively, comprising the steps of
a) identifying a patient in need thereof, and
b) administering a therapeutically effective amount of said pharmaceutical formulation in an aqueous medium.
28. The method of claim 27, wherein said solubilizing agent is selected from the group consisting of α-cyclodextrin, β-cyclodextrin, hydroxypropyl β-cyclodextrin. and/or a mixture of two or more different cyclodextrins.
29. The method of claim 27, wherein said solubilizing agent comprises sulfobutyl ether β-cyclodextrin sodium.
30. The method of claim 29, wherein said compound is perampanel or hydrate thereof.
31. The method of claim 27, wherein the administering step occurs in materials not made of polyvinyl chloride (PVC).
32. The method of claim 27, wherein the pH of the pharmaceutical formulation is between 6 and 8.
33. The method of claim 29, wherein said compound is perampanel in a lyophilized matrix containing 2-6 mg of perampanel and 1500-2500 mg of SBE-β-CD, which when reconstituted with water provides a solution of pH 5 to 9.
34. The method of claim 33, wherein said compound is perampanel in a lyophilized matrix containing 2-6 mg of perampanel and 1500-2500 mg of SBE-β-CD, which when reconstituted with water provides a solution of pH 6 to 8.
35. The method of claim 34, wherein said compound is perampanel in a lyophilized matrix containing 3-5 mg of perampanel and 1900-2100 mg of SBE-β-CD, which when reconstituted with water provides a solution of pH 6 to 8.
36. The method of claim 35, wherein said compound is perampanel in a lyophilized matrix containing 4 mg of perampanel and 2000 mg of SBE-β-CD, which when reconstituted with water provides a solution of pH 6 to 8.

We claim:
1. A pharmaceutical formulation comprising a solubilizing agent and a therapeutically effective amount of perampanel or a hydrate thereof;
wherein said solubilizing agent is a sulfobutyl ether β-cyclodextrin;
wherein said sulfobutyl ether β-cyclodextrin is present in a molar ratio of between 28 to 108 moles per 1 mole perampanel;
wherein the pharmaceutical formulation is in an aqueous solution;
wherein the pharmaceutical formulation has 0.6 mg/mL to 0.8 mg/mL perampanel solution in 30% to 40% sulfobutyl ether β-cyclodextrin by weight;
and a pH in a range of 6 to 8.
2. The pharmaceutical formulation of claim 1, wherein said solubilizing agent is sulfobutyl ether β-cyclodextrin sodium.
3. The pharmaceutical formulation of claim 1, wherein the 0.6 mg/mL to 0.8 mg/mL perampanel solution is prepared from a hydrate of perampanel.
4. The pharmaceutical formulation of claim 3, wherein said perampanel hydrate is perampanel ¾ hydrate.
5. The pharmaceutical formulation of claim 1, wherein the 0.6 mg/mL to 0.8 mg/mL perampanel solution is prepared from perampanel in the amorphous phase.
6. The pharmaceutical formulation of claim 1, wherein the molar ratio is about 81 moles sulfobutyl ether β-cyclodextrin per 1 mole perampanel.
7. The pharmaceutical formulation of claim 1, wherein the pharmaceutical formulation has a pH of 7.
8. A storage-stable aqueous pharmaceutical formulation for intravenous administration comprising an aqueous, supersaturated perampanel solution and sulfobutyl ether β-cyclodextrin,
wherein said sulfobutyl ether β-cyclodextrin is present in a molar ratio of between 60 to 110 moles per 1 mole perampanel; and
wherein the storage-stable aqueous pharmaceutical formulation has 0.6 mg/mL to 0.8 mg/mL perampanel solution in 30% to 40% sulfobutyl ether β-cyclodextrin by weight, and a pH in a range of 6 to 8.
9. The storage-stable aqueous pharmaceutical formulation of claim 8, wherein the molar ratio is about 81 moles sulfobutyl ether β-cyclodextrin per 1 mole perampanel.
10. The storage-stable aqueous pharmaceutical formulation of claim 8, wherein the pharmaceutical formulation has 0.8 mg/mL perampanel solution in 40% sulfobutyl ether β-cyclodextrin.
11. The storage-stable aqueous pharmaceutical formulation of claim 8, wherein the pharmaceutical formulation has 0.6 mg/mL perampanel solution in 30% sulfobutyl ether β-cyclodextrin.

12. The storage-stable aqueous pharmaceutical formulation of claim 8, wherein the pharmaceutical formulation has a pH of 7.

13. A drug product for intravenous administration to a subject comprising a formulation of claim 1.

14. The drug product of claim 13, wherein the drug product has a pH of 7.

15. The drug product of claim 13, wherein the molar ratio is about 81 moles sulfobutyl ether β-cyclodextrin per 1 mole perampanel.

* * * * *